United States Patent
Bharmi et al.

(10) Patent No.: US 8,504,144 B2
(45) Date of Patent: *Aug. 6, 2013

(54) SYSTEMS AND METHODS FOR EMPLOYING MULTIPLE FILTERS TO DETECT T-WAVE OVERSENSING AND TO IMPROVE TACHYARRHYTHMIA DETECTION WITHIN AN IMPLANTABLE MEDICAL DEVICE

(75) Inventors: Rupinder Bharmi, Stevenson Ranch, CA (US); Jeffery D. Snell, Chatsworth, CA (US); Gene A. Bornzin, Simi Valley, CA (US); Joseph J. Florio, Bend, OR (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1268 days.

This patent is subject to a terminal disclaimer.

(21) Appl. No.: 11/776,266

(22) Filed: Jul. 11, 2007

(65) Prior Publication Data
US 2009/0018595 A1 Jan. 15, 2009

(51) Int. Cl.
A61B 5/0452 (2006.01)
A61B 5/0456 (2006.01)
A61B 5/0464 (2006.01)

(52) U.S. Cl.
CPC .............. *A61B 5/0464* (2013.01); *A61B 5/0456* (2013.01)
USPC .......................................... 600/518; 600/521

(58) Field of Classification Search
USPC ................. 607/515, 517–518, 521, 1–2, 4–5, 607/9, 14–15, 17, 25–26; 600/521, 508–510, 600/515–519
See application file for complete search history.

(56) References Cited

U.S. PATENT DOCUMENTS

| | | |
|---|---|---|
| 5,404,880 A | 4/1995 | Throne |
| 5,476,485 A | 12/1995 | Weinberg et al. |
| 5,558,097 A | 9/1996 | Jacobson et al. |
| 5,623,936 A | 4/1997 | McClure |
| 6,249,705 B1 | 6/2001 | Snell |
| 6,772,007 B1 | 8/2004 | Kroll |
| 6,862,471 B1 | 3/2005 | McClure et al. |
| 6,907,286 B1 | 6/2005 | Kroll et al. |
| 7,813,791 B1 * | 10/2010 | Gill et al. ....................... 600/521 |
| 2003/0204215 A1 | 10/2003 | Gunderson et al. |
| 2004/0015197 A1 | 1/2004 | Gunderson |
| 2006/0085038 A1 * | 4/2006 | Linder et al. ...................... 607/4 |
| 2006/0235476 A1 | 10/2006 | Gunderson et al. |
| 2007/0032829 A1 * | 2/2007 | Ostroff ............................. 607/5 |

FOREIGN PATENT DOCUMENTS

| | | |
|---|---|---|
| WO | WO03/092810 | 11/2003 |
| WO | WO2004/093974 | 11/2004 |

OTHER PUBLICATIONS

NonFinal Office Action, mailed Apr. 28, 2011—Related U.S. Appl. No. 11/776,275.

* cited by examiner

*Primary Examiner* — Carl H Layno
*Assistant Examiner* — Jessica Sarcione

(57) ABSTRACT

Techniques for detecting tachyarrhythmia and also for preventing T-wave oversensing use signals filtered by a narrowband bradycardia filter in combination with signals filtered by a narrowband tachycardia filter. A separate wideband filter may also be used.

20 Claims, 26 Drawing Sheets

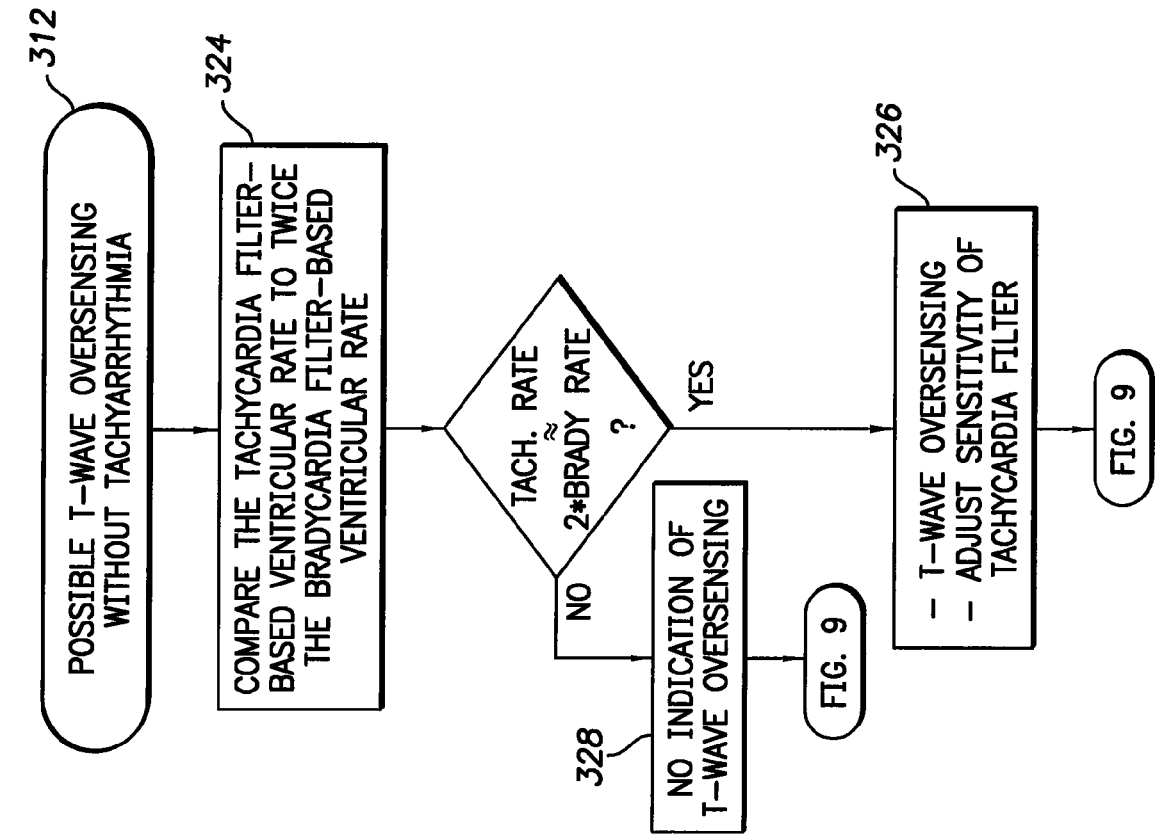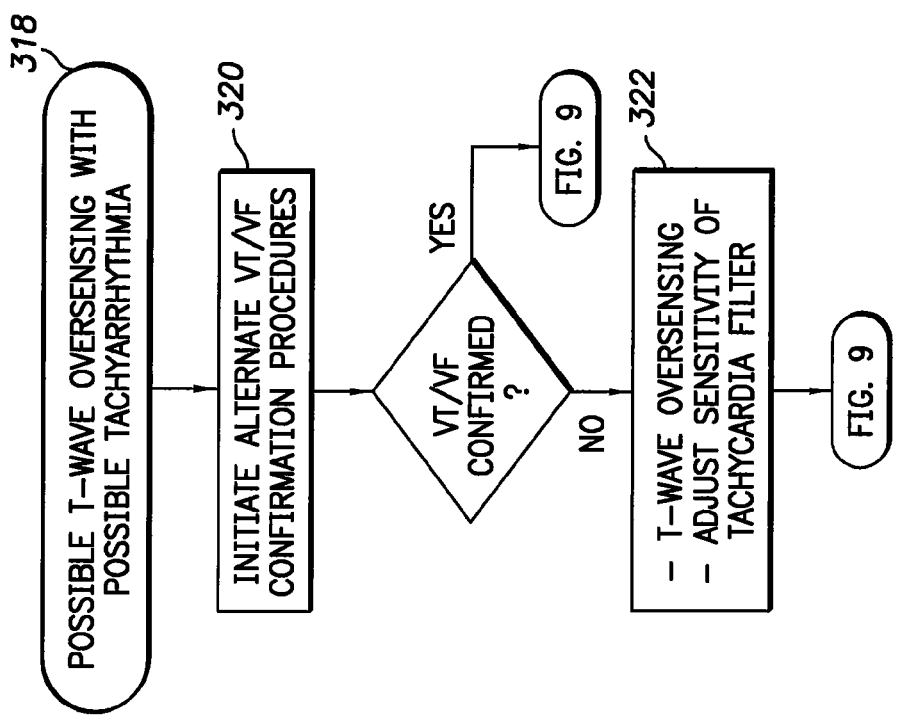
FIG. 11

SYSTEMS AND METHODS FOR EMPLOYING MULTIPLE FILTERS TO DETECT T-WAVE OVERSENSING AND TO IMPROVE TACHYARRHYTHMIA DETECTION WITHIN AN IMPLANTABLE MEDICAL DEVICE

RELATED APPLICATIONS

This application is related to U.S. patent application Ser. No. 11/776,275, filed Jul. 11, 2007 entitled "SYSTEMS AND METHODS FOR EMPLOYING MULTIPLE FILTERS TO DETECT T-WAVE OVERSENSING AND TO IMPROVE TACHYARRHYTHMIA DETECTION WITHIN AN IMPLANTABLE MEDICAL DEVICE", which is fully incorporated by reference herein.

FIELD OF THE INVENTION

The invention generally relates to implantable medical devices such as pacemakers and implantable cardioverter/defibrillators (ICDs) and, in particular, to (1) techniques for detecting ventricular tachyarrhythmia and also to (2) techniques for preventing T-wave oversensing.

BACKGROUND OF THE INVENTION

An arrhythmia is an abnormal heart beat pattern. One example of arrhythmia is bradycardia wherein the heart beats at an abnormally slow rate or wherein significant pauses occur between consecutive beats. Other examples of arrhythmia include tachyarrhythmias wherein the heart beats at an abnormally fast rate. With an atrial tachyarrhythmia, such as atrial tachycardia (AT), the atria of the heart beat abnormally fast. With a ventricular tachyarrhythmia, such as ventricular tachycardia (VT), the ventricles of the heart beat abnormally fast. Though often unpleasant for the patient, a tachycardia is typically not fatal. However, some tachycardias, particularly ventricular tachycardia, can trigger ventricular fibrillation (VF) wherein the heart beats chaotically such that there is little or no net flow of blood from the heart to the brain and other organs. VF, if not terminated, is fatal. Hence, it is highly desirable for implantable medical devices, such as pacemaker or ICDs (herein generally referred to as a pacer/ICD) to detect arrhythmias, particularly ventricular tachyarrhythmias, so that appropriate therapy can be automatically delivered by the device.

To detect arrhythmias, the pacer/ICD senses electrical cardiac signals within the heart of the patient using one or more implanted electrodes. The cardiac signals are sensed within the device by one or more sense amplifiers and then filtered by various filters configured so as to extract signals of interest, such as signals indicative of bradycardia or tachycardia or other arrhythmias. To this end, state-of-the-art pacer/ICD's are often provided with a wideband filter and two narrow bandwidth filters. The wideband filter eliminates low and high frequency noise but otherwise retains all features of the cardiac signals indicative of actual electrical events within the heart of the patient. That is, the wideband filter retains P-waves, R-waves and T-waves, whether occurring at normal heart rates, excessively low rates, or excessively high rates. The P-wave is the portion of an electrical cardiac signal that is representative of the electrical depolarization of the atria and is thus also representative of the physical contraction of the atria. The R-wave—which is a part of a QRS complex—is the portion of an electrical cardiac signal that is representative of the electrical depolarization of the ventricles and is thus also representative of the physical contraction of the ventricles. The T-wave is the portion of an electrical cardiac signal that is representative of the electrical repolarization of the ventricles. Note that the repolarization of the atria typically generates electrical signals that are too weak to be detected and hence atrial repolarization events are not typically detected. Hence, within the wideband cardiac signals, the P-wave is typically followed by the R-wave, which is then followed by the T-wave. Note, however, that the wideband filter also retains signals associated with any chaotic or random beating of the chambers of the heart, particularly signals associated with VF, which may not be easily categorized as having discrete P-waves, R-waves or T-waves. Also, note that, P-waves, R-waves and T-waves are also features of a surface electrocardiogram (EKG), though the corresponding features of the EKG often differ in shape and magnitude from those of the IEGM.

FIG. 1 provides a stylized illustration of a cardiac signal 2 corresponding to a single heartbeat, particularly illustrating the P-wave 4, R-wave 6, and the T-wave 8. In practice, the relative magnitudes of the various events can differ significantly. In some cases, the T-wave may be as large as or larger than the R-wave. Accordingly, it can be difficult to obtain an accurate measure of the ventricular rate from the wideband-filtered signals and so it can be difficult to reliably detect either bradycardia or tachycardia from the wideband-filtered signals. Hence, the specialized narrowband filters have been developed. Initially, a narrowband "bradycardia filter" was provided within pacemakers that passed (or "retained") only R-waves for the purposes of detecting bradycardia. If the rate at which R-waves appear in the filtered signal is below a lower rate threshold, or if no R-waves are present at all in the filtered signal, then the patient is likely suffering an episode of bradycardia, and appropriate therapy is delivered, such as demand-based pacing. Although effective for detecting bradycardia, the filter also eliminates R-waves associated with VF, i.e. the bradycardia filter also filtered out V-fib waves. ICDs need to reliably detect VF for the purposes of delivering defibrillation shocks. Hence, a narrowband "tachycardia" filter was also developed that had a wider passband for the purposes of also detecting R-waves or V-fib waves associated with VF/VT. If the rate at which R-waves appear in the tachycardia-filtered signal is above a VT threshold, then the patient is likely suffering an episode of VT, and appropriate therapy can be delivered, such as antitachycardia pacing (ATP). If the rate exceeds a higher VF threshold, or if V-fib waves are detected, then the patient is likely suffering an episode of VF, and defibrillation shocks are delivered.

Accordingly, many state-of-the art pacer/ICDs now include both a bradycardia filter and a tachycardia filter. Advantageously, because T-waves are filtered out by the bradycardia filter, the sensitivity of the bradycardia filter can be set quite high so as to permit detection of even very low amplitude R-waves. The high sensitivity of the bradycardia filter thus substantially eliminates the risk of any possible undersensing of the R-waves (or at least any significant undersensing of relatively low rate R-waves.) Herein, "undersensing" refers to the failure to detect events of interest that are actually present within the raw cardiac signals. Meanwhile, the elimination of T-waves means that there is substantially no risk of "oversensing" when using the bradycardia filter. Herein, "oversensing" refers to the erroneous detection of an event not actually present in the raw cardiac signal, such as the detection of R-waves that are not in fact present. Oversensing typically arises when one event is misidentified as another, as may occur, e.g., if a T-wave is improperly identified as an R-wave. As can be appreciated, T-wave oversensing is a significant concern since misidentification of T-waves as R-waves can result in significant miscalculation of the true heart rate within the patient, causing therapy to be delivered when not warranted or potentially causing therapy to be withheld even when needed. Insofar as bradycardia is concerned, T-wave oversensing might result in a failure to detect bradycardia since misidentification of T-waves as R-waves would result in a significantly higher heart rate being detected than actually occurring within the patient. As noted, the bradycardia filter is configured to substantially eliminate all T-waves so that T-wave oversensing is not a concern on the bradycardia channel. Hence, the state-of-the art pacer/ICD can reliably use the bradycardia filter to detect bradycardia.

FIG. 2 illustrates the operation of the bradycardia filter during normal sinus rhythm. A first graph 10 of the figure illustrates the output of the wideband filter, particularly highlighting that portion of the filtered signal corresponding to the location of T-waves 12. Note that, in the figure, T-waves corresponding to numerous heartbeats are shown superimposed over one another. The vertical axis of the graph illustrates the magnitude, in arbitrary units, relative to an iso-electric baseline. The horizontal axis illustrates the time delay in milliseconds (ms) from the preceding R-wave. A portion of each preceding R-wave appears within the graph around time: 0 ms. A portion of each subsequent R-wave appears within the graph as well, beginning at about 500 ms. Between them, T-waves are clearly seen.

Meanwhile, a second graph 14 of FIG. 2 illustrates the output of the bradycardia filter. Again, cardiac signals corresponding to numerous heartbeats are shown superimposed over one another. As can be seen, T-waves are completely eliminated within the bradycardia signals, leaving only those portions corresponding to R-waves (again seen at the beginning and at the end of the highlighted section of the cardiac signal.) By completely eliminating the T-wave, the ventricular rate can be easily and accurately measured based solely on the R-waves (at least at relatively low heart rates), and hence bradycardia can be reliably detected from the filtered signals.

However, unlike the bradycardia filter, which fully eliminates T-waves, the tachycardia filter retains T-waves. This is due to the fact that the frequencies associated with the V-fib waves of interest are also associated with T-waves, and hence the filter cannot eliminate all T-waves while still retaining the V-fib waves. As such, the sensitivity of the tachycardia filter must be set so as to detect high rate R-waves and V-fib waves while eliminating T-waves. This is difficult, at best, since the relative magnitudes of the R-waves, V-fib waves and T-waves may change significantly over time within the patient, perhaps due to the use of medications or due to physiological or anatomical changes in the heart brought on by medical conditions, such as cardiac ischemia, myocardial infarctions, congestive heart failure, etc. Moreover, as already noted, T-waves can sometimes have a magnitude that equals or exceeds that of the R-wave. Hence, T-wave oversensing is a significant problem within the tachycardia-filtered signals.

FIG. 3 illustrates the operation of a tachycardia filter during VT/VF. A first graph 16 illustrates the output of the wideband filter, again particularly highlighting that portion of the filtered signal corresponding to the location of T-waves 18. Note that, as in the previous figure, T-waves corresponding to numerous heartbeats are shown superimposed over one another. The vertical axis of the graph again illustrates magnitude relative to an iso-electric baseline. The horizontal axis again illustrates the time delay from the preceding R-wave. A portion of each preceding R-wave appears within the graph around time: 0 ms-10 ms. A portion of each subsequent R-wave appears within the graph as well, beginning at about 60 ms. Between them, T-waves 18 are clearly seen. (As a result of variations in R-R intervals occurring during VT, the R-waves and T-waves from different heartbeats are not aligned with one another within the graph, as was the case in FIG. 1.)

Meanwhile, a second graph 20 of FIG. 2 illustrates the output of the tachycardia filter. Again, cardiac signals corresponding to numerous heartbeats are shown superimposed over one another. As can be seen, T-waves 22 are not completely eliminated within the tachycardia-filtered signals, leaving signals that might be misidentified as R-waves, particularly if the sensitivity of the tachycardia filter is set too high. That is, T-wave oversensing might occur. Without complete elimination of the T-wave, the ventricular rate cannot be accurately and reliably measured based solely on the output of the tachycardia filter (at least at the rates associated with VT/VF), and hence problems arise in the detection of VT/VF or other forms of ventricular tachyarrhythmia. Failure to properly detect VT/VF when it is present can result in a failure to deliver appropriate therapy. False detection of VT/VF when it is not present can result in delivery of inappropriate therapy. As can be appreciated, both situations are of significant concern.

In view of the problems arising when using a narrowband tachycardia filter, it is highly desirable to provide improved techniques for reliably detecting VT/VF that may be performed by a pacer/ICD. It is to this end that various aspects of the invention are generally directed. It is particularly desirable to provide improved techniques that do not require replacement or elimination of existing tachycardia filters, but that instead achieve improved VT/VF detection when using otherwise conventional tachycardia filters. It is to this end that particular aspects of the invention are directed.

Still further aspects of the invention are directed to providing improved techniques for detecting and eliminating T-wave oversensing, even in the absence of any arrhythmia. Heretofore, at least some techniques for addressing T-wave oversensing have been directed to providing blanking intervals synchronized with the expected location of the T-wave. See, for example, U.S. Pat. No. 6,862,471 to McClure, et al., entitled "Method and Apparatus for Blanking T-Waves from Combipolar Atrial Cardiac Signals based on Expected T-Wave Locations." It would be desirable to provide techniques for detecting and eliminating T-wave oversensing that do not necessarily require the use of blanking intervals, and various aspects of the invention are directed to that end as well.

SUMMARY OF THE INVENTION

In a first general embodiment of the invention, a method is provided for detecting tachyarrhythmia within a patient in which an implantable medical device is implanted, where the device is equipped to process electrical cardiac signals sensed via leads implanted within the patient and wherein the device has a first filter operative to substantially eliminate signals having frequencies associated with ventricular repolarization events while retaining signals having frequencies associated with at least some ventricular depolarization events and a second filter operative to pass signals having frequencies associated with ventricular depolarization events and ventricular repolarization events. In the illustrative embodiments described herein, the first filter is referred to as a bradycardia filter and the second filter is referred to as a tachycardia filter.

The first general embodiment comprises: sensing electrical cardiac signals within the patient; selectively filtering the signals using the bradycardia filter and the tachycardia filter; and then detecting tachyarrhythmia within the patient using signals filtered by the bradycardia filter in combination with signals filtered by the tachycardia filter. In other words, a tachyarrhythmia, such as VT, is detected based on a combination of bradycardia-filtered signals and tachycardia-filtered signals. This is in contrast with the predecessor techniques described above, wherein tachycardia is detected using only those signals sensed by the tachycardia filter.

In a first illustrative example of the first general embodiment of the invention, tachyarrhythmia is detected using signals filtered by the bradycardia filter in combination with signals filtered by the tachycardia filter by: detecting a preliminary indication of tachyarrhythmia using signals filtered by the bradycardia filter; and, in response, confirming the detection of tachyarrhythmia using signals filtered by the tachycardia filter. That is, the bradycardia filter, which is traditionally used only to detect bradycardia, is additionally used to detect a preliminary indication of a tachyarrhythmia, such as VT. If such a preliminary indication is detected, the tachycardia filter is then activated to confirm the detection of the tachyarrhythmia, before therapy is delivered. In this manner, the tachycardia filter need not run continuously, but is instead activated only when there is some indication of possible tachyarrhythmia, and hence power is saved. In one specific example, a single filter is employed that is capable of being programmed to operate as either a bradycardia filter or a tachycardia filter. By default, it operates as a bradycardia filter. If an indication of tachyarrhythmia is detected, it is then reprogrammed to instead operate as a tachycardia filter. In this manner, a single reconfigurable filter can be used to perform the functions of both bradycardia filtering and tachycardia filtering, thus saving device resources.

In the first illustrative example, the preliminary indication of tachyarrhythmia may be detected by analyzing ventricular channel signals filtered by the bradycardia filter to detect one or more of: a ventricular rate that exceeds a predetermined VT detection threshold; the presence of a significant number of ventricular depolarization events of irregular shape; the presence of a significant number of ventricular depolarization events of irregular size; the presence of a significant number of ventricular depolarization events occurring at a rate below the VT detection threshold but above a rate consistent with normal sinus rhythm; or the lack of ventricular depolarization events, wherein the lack of ventricular depolarization events is not consistent with bradycardia (as may occur during VF.) Once a preliminary indication of tachyarrhythmia has been detected, ventricular channel signals filtered by the tachycardia filter are then analyzed to confirm the ventricular tachyarrhythmia by, e.g., determining a ventricular rate using the signals filtered by the tachycardia filter and then verifying that the ventricular rate exceeds the VT detection threshold.

In a second illustrative example of the first general embodiment of the invention, tachyarrhythmia is detected using signals filtered by the bradycardia filter in combination with signals filtered by the tachycardia filter by: filtering ventricular channel signals sensed via the leads using the tachycardia filter while also filtering ventricular channel signals sensed via the leads using the bradycardia filter; and then comparing the ventricular channel signals filtered by the tachycardia filter and the bradycardia filter to detect ventricular tachyarrhythmia. In other words, in this embodiment, the bradycardia and tachycardia filters preferably operate simultaneously to filter the same signals. The filtered signals are compared to detect the tachyarrhythmia. In one particular example, ventricular tachyarrhythmia is detected by: (1) determining a tachycardia filter-based ventricular rate from the signals filtered by the tachycardia filter while also determining a bradycardia filter-based ventricular rate from the signals filtered by the bradycardia filter; (2) comparing the tachycardia filter-based ventricular rate to a predetermined VT detection threshold; (3) comparing the tachycardia filter-based ventricular rate to the bradycardia filter-based ventricular rate; and (4) detecting a ventricular tachyarrhythmia if the tachycardia filter-based ventricular rate is greater than the VT threshold and if the tachycardia filter-based ventricular rate is also greater than twice the bradycardia filter-based ventricular rate. If so, VT therapy is immediately delivered. If, instead, the tachycardia filter-based ventricular rate is greater than the VT threshold but not greater than twice the bradycardia filter-based ventricular rate, then additional confirmation procedures are employed to verify the VT before therapy is delivered. If, alternatively, the tachycardia filter-based ventricular rate is not greater than the VT threshold but is about equal to twice the bradycardia filter-based ventricular rate, then an indication of T-wave oversensing is generated.

In this regard, if the ventricular rate derived from the tachycardia filter is about equal to twice the ventricular rate derived bradycardia filter, the tachycardia filter rate is likely due to T-wave oversensing, i.e. each T-wave is being misidentified as an R-wave, yielding a rate double that of the bradycardia filter. In that case, tachycardia is probably not actually occurring and so an indication of T-wave oversensing by the tachycardia filter is generated. Nevertheless, if the ventricular rate is above the VT threshold then, to be safe, VT confirmation procedures are preferably initiated to determine whether a tachycardia might be occurring and, if so, appropriate therapy is delivered. However, if the ventricular rate derived from the tachycardia filter is above the VT threshold and is also greater than twice the ventricular rate derived bradycardia filter, then tachycardia is almost certainly occurring, since T-wave oversensing, by itself, would not produce such a result. Accordingly, as set forth in step (4) above, if the ventricular rate derived from the tachycardia filter is greater than the VT threshold and if the ventricular rate derived from the tachycardia filter is also greater than twice the ventricular rate derived from the bradycardia filter, then VT is immediately detected, i.e. no further confirmation is required, and so therapy is promptly delivered. Also, note that, if the rate derived from the tachycardia filter is well below the VT threshold and is also about equal to the rate derived from the bradycardia filter, then normal sinus rhythm is occurring without T-wave oversensing and so no action need be taken.

This logic is summarized in Table I. (Note that not all possible logic combinations of the parameters are set forth in the Table. Rather, only those logic combinations that are pertinent to the second illustrative example are set forth.)

TABLE I

| Tachycardia Filtered Rate versus VT Threshold | Tachycardia Filtered Rate versus Bradycardia Filtered Rate | Result |
|---|---|---|
| Tachycardia Rate > VT Threshold | Tachycardia Rate > 2 * Bradycardia Rate | → VT Immediately Detected; Deliver Therapy |
| Tachycardia Rate > VT Threshold | Tachycardia Rate ≦ 2 * Bradycardia Rate | → Possible T-wave oversensing; Possible VT; Initiate VT/VT Confirmation Procedure Before Delivering Therapy |

TABLE I-continued

| Tachycardia Filtered Rate versus VT Threshold | Tachycardia Filtered Rate versus Bradycardia Filtered Rate | Result |
|---|---|---|
| Tachycardia Rate ≦ VT Threshold | Tachycardia Rate ≈ 2 * Bradycardia Rate | → T-wave Oversensing; Adjust Tachycardia Filter Sensitivity |
| Tachycardia Rate << VT Threshold | Tachycardia Rate ≈ Bradycardia Rate | → No T-wave Oversensing Normal Sinus Rhythm |

Thus, with this implementation, by simultaneously using both a bradycardia and a tachycardia filter and comparing the two filtered signals to one another, very prompt detection of VT can be achieved, while also detecting possible T-wave oversensing.

In a third illustrative example of the first general embodiment of the invention, tachyarrhythmia is detected by: filtering ventricular channel signals sensed via the leads using the tachycardia filter; detecting a preliminary indication of tachyarrhythmia using the signals filtered by the tachycardia filter; and, in response, confirming the detection of tachyarrhythmia by comparing additional signals filtered by the tachycardia filter with additional signals filtered by the bradycardia filter. The logic summarized above may be exploited to confirm the detection of tachyarrhythmia using the signals filtered by the tachycardia filter and the signals filtered by the bradycardia filter. In other words, this embodiment is similar to the second illustrative example, but the tachycardia filter is used to detect a preliminary indication of tachyarrhythmia before any bradycardia-filtered signals are compared against tachycardia-filtered signals. The preliminary indication may be used, e.g., to trigger charging of defibrillation capacitors in the case that a defibrillation shock is ultimately required. The preliminary indication of tachyarrhythmia may be detected by determining a ventricular rate based on the signals filtered by the tachycardia filter and comparing that rate against a VT threshold. In any case, by performing the comparison of the bradycardia filtered signals and the tachycardia-filtered signals only if a preliminary indication of tachyarrhythmia has already been made, such a comparison need not be performed in the absence of possible tachyarrhythmia.

In a fourth illustrative example of the first general embodiment of the invention, tachyarrhythmia is detected by: comparing ventricular channel signals filtered by the bradycardia filter with ventricular channel signals filtered by the tachycardia filter to distinguish between "true" ventricular events and "false" ventricular events; and then detecting tachyarrhythmia based on the true ventricular depolarization events. In one example, true ventricular depolarization events are distinguished from false ventricular depolarization events by: filtering ventricular channel signals using the bradycardia filter and identifying ventricular events therein; filtering ventricular channel signals using the tachycardia filter and identifying ventricular events therein; detecting a first ventricular event in either of the filtered signals; determining whether a second ventricular event occurs within the signals filtered by the tachycardia filter within a predetermined time window following the first event; and if so, identifying the second event as being a false ventricular depolarization event indicative of tachycardia-filter oversensing, and if not, identifying the second event as being indicative of a true ventricular depolarization event. In other words, following detection of an event within the tachycardia filtered either signals or the bradycardia-filtered signals, the device opens up a detection window. If another event is detected within the tachycardia-filtered signals within that detection window, the second event is rejected as being a T-wave. Otherwise, the second event is deemed to be a true R-wave. The time window may be, for example, set in the range of 50-150 ms.

In one example, tachyarrhythmia is detected based on the true ventricular depolarization events by calculating a ventricular rate based only on true R-waves and comparing that rate to a VT threshold. In another example, tachyarrhythmia is detected based on all ventricular events by: determining a ventricular rate based on all detected ventricular events (i.e. true and false depolarization events); counting a number of false ventricular depolarization events within a predetermined number of combined false and true depolarization events; generating an indication of tachycardia filter-oversensing if the count exceeds a predetermined count threshold indicative of tachycardia filter-oversensing; and then detecting ventricular tachyarrhythmia if the ventricular rate exceeds a VT threshold and the count does not exceed the predetermined count threshold. For example, if at least seven false R-waves are detected out of every ten total R-waves, then T-wave oversensing is deemed to be occurring and so ventricular tachyarrhythmia is not initially indicated, even if the rate exceeds the VT threshold, due to the significant T-wave oversensing. Preferably, confirmation procedures are then employed to determine whether VT is nevertheless occurring, despite the T-wave oversensing.

In another example, the step of comparing ventricular channel signals filtered by the bradycardia filter with ventricular channel signals filtered by the tachycardia filter to distinguish between true ventricular depolarization events and false ventricular depolarization events is performed only in response to detection of a preliminary indication of tachyarrhythmia made using the tachycardia filter. In yet another example, the steps of (a) comparing ventricular channel signals filtered by the bradycardia filter with ventricular channel signals filtered by the tachycardia filter to distinguish between true ventricular depolarization events and false ventricular depolarization events and (b) detecting tachyarrhythmia based on the true ventricular depolarization events are only performed during a "confirmation period" following the preliminary detection of tachyarrhythmia made using the tachycardia filter. The confirmation period may extend, e.g., for 100 ventricular event cycles following that preliminary detection. That is, upon detection of a possible VT made using the tachycardia filter, the device then seeks to confirm the arrhythmia using both the tachycardia and bradycardia filters during the next 100 cardiac cycles. If the arrhythmia is confirmed during that period of time, therapy is delivered promptly. If the arrhythmia is disconfirmed during that period of time (due to detection of significant T-wave oversensing), therapy is not delivered. To be safe, if thereby is neither confirmed nor disconfirmed during that period of time, but the ventricular rate remains above the VT threshold, therapy is promptly delivered at the end of that period of time. This ensures that therapy is delivered in circumstances where it may not be clear whether T-wave oversensing is occurring or not.

In a fifth illustrative example of the first general embodiment of the invention, wherein the device additionally includes a wideband filter having a substantially wider bandwidth than bandwidths of the bradycardia and tachycardia filters, tachyarrhythmia is detected using signals filtered by the wideband filter in combination with signals filters by the bradycardia and tachycardia filters. That is, all three filters are exploited. In one example, tachyarrhythmia is detected by: identifying possible ventricular depolarization events within signals filtered, respectively, by the wideband filter, the bradycardia filter, and the tachycardia filter; comparing the timing of the possible ventricular depolarization events identified within the respective filtered signals to identify true ventricular depolarization events; and then detecting ventricular tachyarrhythmia based on the true ventricular depolarization events.

In this regard, events that occur substantially contemporaneously within signals filtered by the wideband filter, the bradycardia filter, and the tachycardia filter are identified as being true ventricular depolarization events. Events that occur substantially contemporaneously within signals filtered by the wideband filter and the tachycardia filter but not the bradycardia filter are identified as being "tachycardia filter-based anomalous events" indicative of (a) a possible ventricular repolarization event (i.e. T-wave) oversensed on the tachycardia filter or (b) a possible ventricular depolarization event (i.e. R-wave) occurring during VF. In response to a tachycardia filter-based anomalous event, the device determines if a ventricular rate derived from the wideband filter is consistent with VF and, if so, the device delivers VF therapy and, if not, the device rejects the anomalous event for the purposes of ventricular rate calculation as being an oversensed ventricular repolarization event (i.e. a T-wave) and then adjusts the sensitivity of the tachycardia filter to reduce oversensing. Events that occur substantially contemporaneously within signals filtered by the wideband filter and the bradycardia filter but not the tachycardia filter are identified as being "bradycardia filter-based anomalous events" indicative of possible tachycardia-filter undersensing. In response to tachycardia filter undersensing, the device adjusts the sensitivity of the tachycardia filter to reduce such undersensing. If an event is detected on the wideband filter, but not on either the tachycardia filter or the bradycardia filter, that event is ignored as either noise or a far-field P-wave.

This logic is summarized in Table II. (Although not shown in the table, in the unlikely event that an event is detected on both the bradycardia and tachycardia filters but not on the wideband filter, that event ignored as an anomalous event, likely arising due to noise on the bradycardia and tachycardia channels.)

TABLE II

| Wideband Filtered Signal | Tachycardia Filtered Signal | Bradycardia Filtered Signal | Result |
|---|---|---|---|
| Event Detected | Event Detected | Event Detected | → True R-wave |
| Event Detected | Event Detected | Event Not Detected | → possible T-wave oversensed with the tachycardia filter possible R-wave occurring during VF |
| Event Detected | Event Not Detected | Event Detected | → Possible tachycardia filter undersensing |
| Event Detected | Event Not Detected | Event Not Detected | → Noise or far-field P-wave on wideband filter |

Thus, a variety of techniques are provided for detecting ventricular tachyarrhythmias. Various aspects of the invention can potentially be extended to detecting atrial tachyarrhythmias as well. Also, the various techniques can be selectively combined to further improve the specificity with which arrhythmias are detected. The various techniques may be implemented, where appropriate, as systems, methods or other appropriate embodiments.

In a second general embodiment of the invention, a method is provided for detecting the oversensing of ventricular repolarization events (i.e. T-waves) within a patient in which an implantable medical device is implanted, where the device is equipped to process electrical cardiac signals sensed via leads implanted within the patient and wherein the device has both a bradycardia filter and a tachycardia filter for filtering the signals. The second general embodiment comprises: sensing electrical cardiac signals within the patient; selectively filtering the signals using a bradycardia filter and a tachycardia filter; and detecting the oversensing of ventricular repolarization events within the signals filtered by the tachycardia filter by comparing the signals filtered by the tachycardia filter with the signals filtered by the bradycardia filter. In other words, T-wave oversensing is detected based on a combination of bradycardia-filtered signals and tachycardia-filtered signals. This is in contrast with the predecessor designs described above, wherein blanking intervals are employed.

In a first illustrative example of the second general embodiment of the invention, the signals are selectively filtered using the bradycardia filter and the tachycardia filter by filtering ventricular channel signals using the bradycardia filter and determining a bradycardia filter-based ventricular rate, and also filtering ventricular channel signals using the tachycardia filter and determining a tachycardia filter-based ventricular rate. The oversensing of T-waves is detected by comparing the tachycardia filter-based ventricular rate to the bradycardia filter-based ventricular rate, and then detecting oversensing of ventricular repolarization events within signals filtered by the tachycardia filter by determining if the tachycardia filter-based ventricular rate is about twice the bradycardia filter-based ventricular rate. In this regard, if T-wave oversensing is occurring, each T-wave may be misidentified as an R-wave, resulting in a tachycardia-filtered ventricular rate about twice that of the bradycardia-filtered ventricular rate. Accordingly, if the tachycardia filter-based ventricular rate is about twice the bradycardia filter-based ventricular rate T-wave oversensing is almost certainly occurring. See Table II above.

In a second illustrative example of the second general embodiment of the invention, the signals are selectively filtered using the bradycardia filter and the tachycardia filter by filtering ventricular channel signals using the bradycardia filter and identifying ventricular events therein, and also filtering ventricular channel signals using the tachycardia filter and identifying ventricular events therein. The oversensing of T-waves is detected by determining, upon detection of a first ventricular event either in the signals filtered by the bradycardia filter or in the signals filtered by the tachycardia filter, whether a second ventricular event is detected in the signals filtered by the tachycardia filter within a predetermined time window following the first event. If so, the second event is identified as being a false ventricular depolarization event indicative of tachycardia-filter oversensing. If not, the second event is identified as being indicative of a true ventricular depolarization event. In other words, following detection of an R-wave within either the tachycardia-filtered signals or the bradycardia-filtered signals, the device opens up a detection window. If another R-wave is detected within the tachycardia-filtered signals within that detection window, the second R-wave is rejected as being a T-wave. Otherwise, the second R-wave is deemed to be a true R-wave. The time window may be, for example, set in the range of 50-150 ms. Similar techniques are discussed above in connection with tachyarrhythmia detection under the fourth illustrative example of the first general embodiment of the invention.

In a third illustrative example of the second general embodiment of the invention, wherein the device additionally includes a wideband filter having a substantially wider bandwidth than bandwidths of the bradycardia and tachycardia filters, the oversensing of T-waves is detected by identifying possible ventricular depolarization events (R-waves) within signals filtered, respectively, by the wideband filter, the bradycardia filter, and the tachycardia filter; and then by comparing the timing of the possible ventricular depolarization events identified within the respective filtered signals to identify oversensed ventricular repolarization events. In one example, the timing of the possible ventricular depolarization events is compared to identify oversensed ventricular repolarization events by identifying events that occur substantially contemporaneously within signals filtered by the wideband filter, the bradycardia filter, and the tachycardia filter as being true ventricular depolarization events. Such events are deemed to be ventricular depolarization events (i.e. R-waves) and not oversensed T-waves. In another example, the timing of the possible ventricular depolarization events is compared to identify oversensed ventricular repolarization events by: identifying events that occur substantially contemporaneously within signals filtered by the wideband filter and the tachycardia filter but not the bradycardia filter as being a tachycardia filter-based anomalous event indicative of one or more of (a) a possible ventricular repolarization event (T-wave) oversensed on the tachycardia filter and (b) a possible ventricular depolarization event (R-wave) occurring during ventricular fibrillation (VF). In response to a tachycardia filter-based anomalous event, the device determines if a ventricular rate derived from the wideband filter is consistent with VF and, if so, delivers VF therapy and, if not, rejects the anomalous event from ventricular rate calculation as being an oversensed ventricular repolarization event (T-wave). Similar techniques are discussed above in connection with tachyarrhythmia detection under the fifth illustrative example of the first general embodiment of the invention.

Thus, a variety of techniques are provided for detecting T-wave oversensing. The various techniques can be selectively combined to further improve the specificity with which T-wave oversensing is detected. The various techniques may be implemented, where appropriate, as systems, methods or other appropriate embodiments. The T-waves oversensing detection techniques and the tachyarrhythmia detection techniques may be combined, as already set forth in the preceding summary.

BRIEF DESCRIPTION OF THE DRAWINGS

The above and further features, advantages and benefits of the invention will be apparent upon consideration of the descriptions herein taken in conjunction with the accompanying drawings, in which:

FIG. 11 particularly illustrates techniques for addressing possible T-wave oversensing for use with the techniques of FIG. 10;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
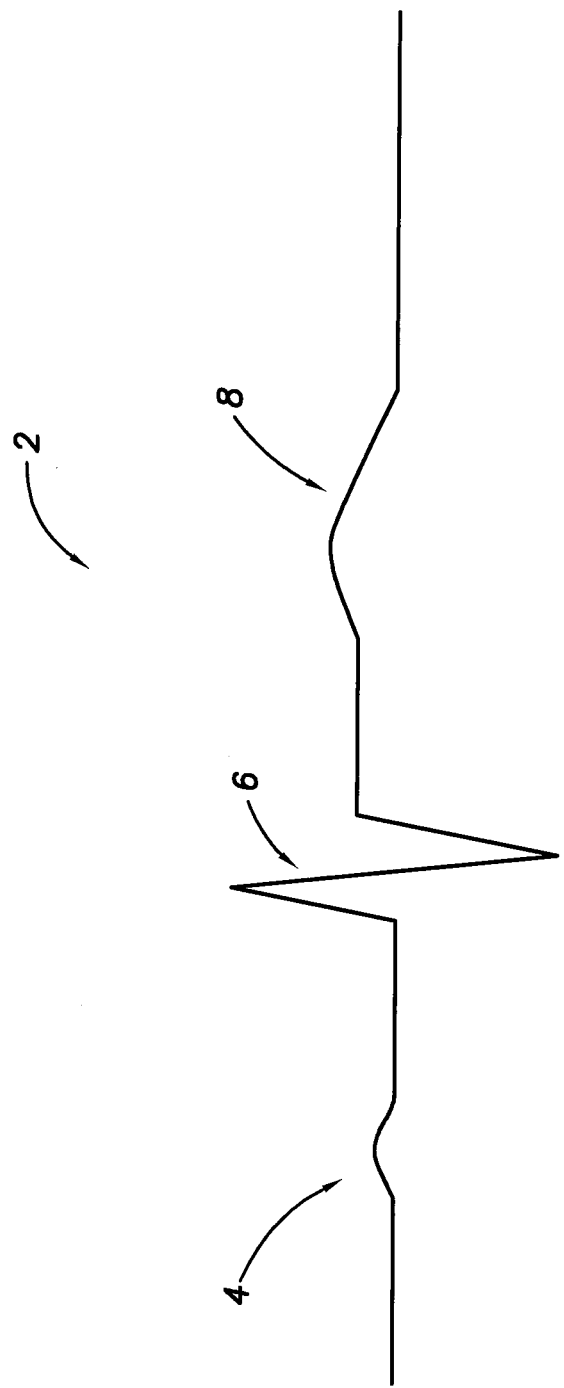
FIG. 1 is a graph illustrating a cardiac signal, particularly identifying P-waves, R-waves, and T-waves therein.
Figure 2:
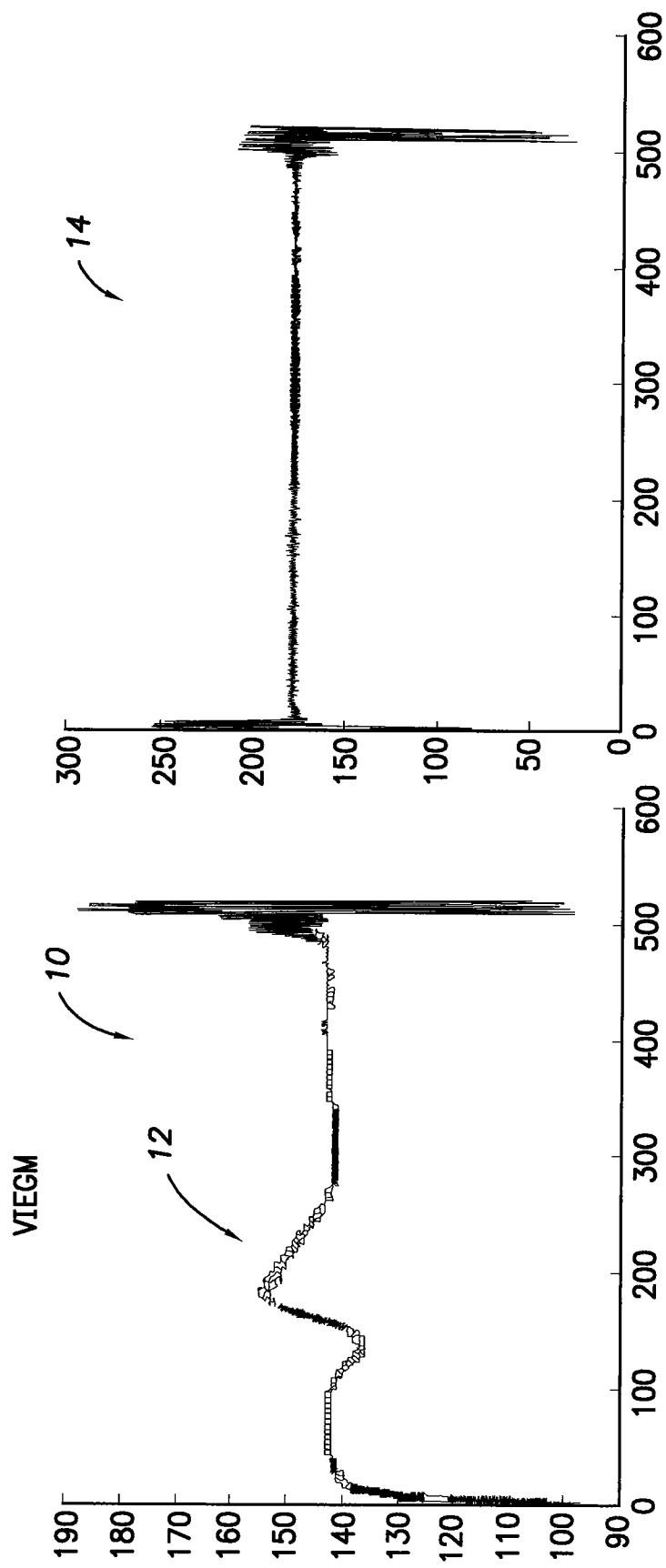
FIG. 2 includes graphs of exemplary filtered cardiac signals illustrating the operation of a wideband filter and a narrowband bradycardia filter, and particularly illustrating the complete filtering of T-waves by the bradycardia filter.
Figure 3:
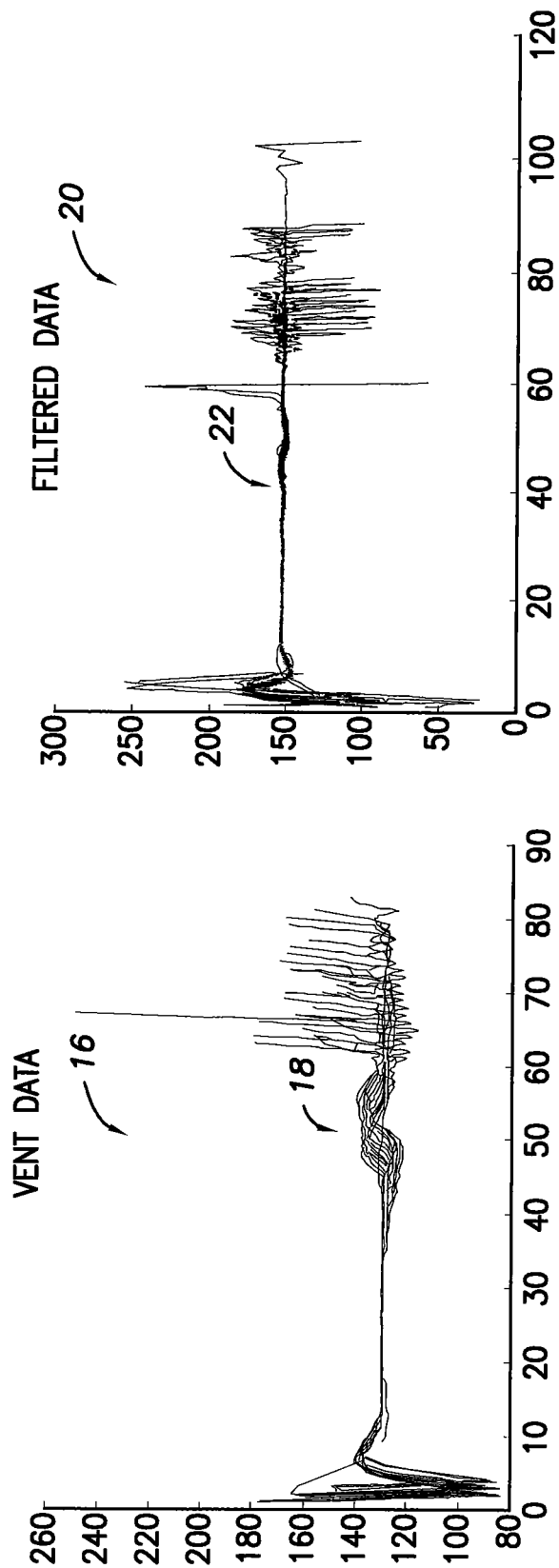
FIG. 3 includes graphs of exemplary filtered cardiac signals illustrating the operation of the wideband filter and a narrowband tachycardia filter, and particularly illustrating the partial filtering of T-waves by the tachycardia filter.
Figure 4:
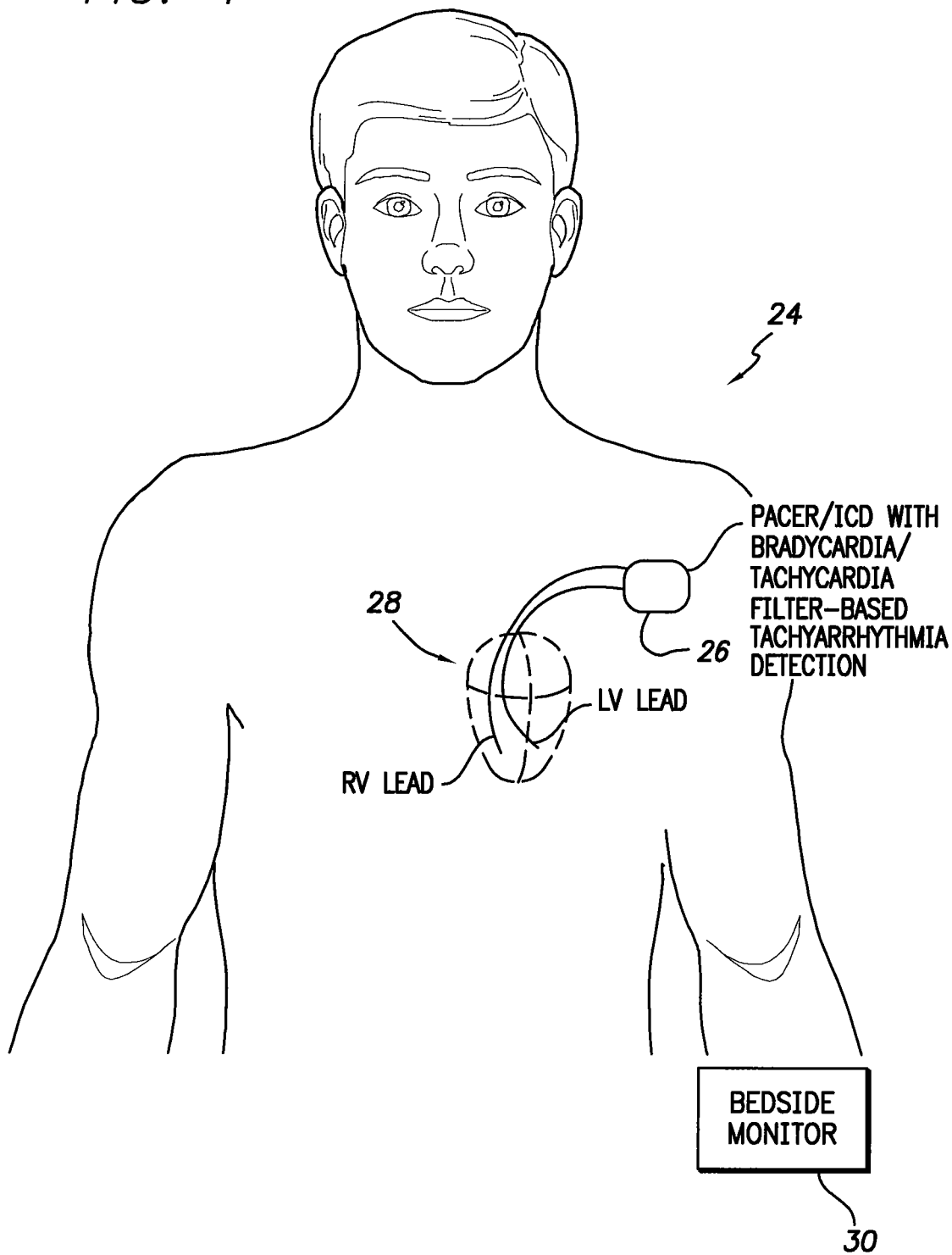
FIG. 4 illustrates pertinent components of an implantable medical system having a pacer/ICD capable of detecting tachyarrhythmias based on signals filtered using a narrowband bradycardia filter (FIG. 2) in combination with signals filtered using a narrowband tachycardia filter (FIG. 3) and capable of delivering therapy in response thereto, and further capable of detecting T-wave oversensing also based on signals filtered using the narrowband bradycardia filter in combination with signals filtered using a narrowband tachycardia filter.
Figure 23:
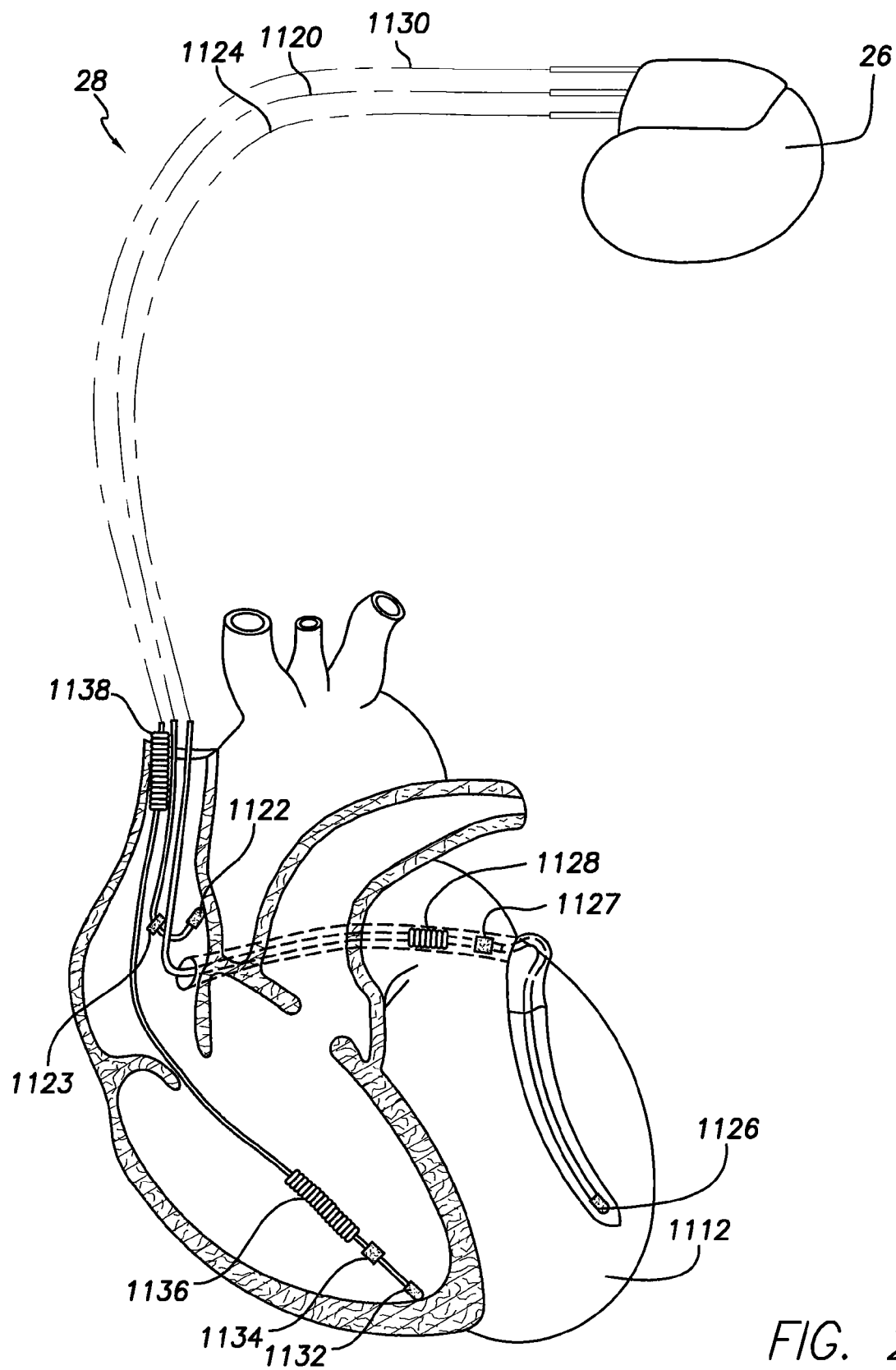
FIG. 23 is a simplified, partly cutaway view, illustrating the pacer/ICD of FIG. 4 along with a set of leads implanted in the heart of a patient.

FIG. 4 illustrates an implantable medical system 24 having a pacer/ICD that includes a bradycardia/tachycardia filter-based tachyarrhythmia detection system, i.e., a system capable of detecting tachyarrhythmias based on signals filtered using a narrowband bradycardia filter in combination with signals filtered using a narrowband tachycardia filter, and also capable of detecting T-wave oversensing based on signals from the narrowband bradycardia and tachycardia filters. To this end, pacer/ICD 26 receives voltage signals from various cardiac pacing leads 28 (only two of which are shown in the FIG. 4) from which various channels of cardiac signals (herein referred to as intracardiac electrogram (IEGM) signals) are derived including, for example, unipolar or bipolar atrial IEGM (A-IEGM) signals and unipolar or bipolar ventricular IEGM (V-IEGM) signals. A complete set of exemplary pacing leads are shown in FIG. 23 from which a wide variety of specific channels of IEGM signals may be derived. The signals are selectively filtered using a narrowband bradycardia filter and a narrowband tachycardia filter to generate filtered signals by which tachyarrhythmia is detected and T-wave oversensing is detected. That is, the bradycardia filter is exploited (in combination with the tachycardia filter) to detect tachyarrhythmias and also to detect T-wave oversensing occurring on tachycardia filtered channels. As will be explained below, a wideband filter may be exploited as well, both in the detection of tachyarrhythmias and in the detection of T-wave oversensing.

The pacer/ICD is also capable of delivering therapy in response to tachyarrhythmias, such as delivery of antitachycardia pacing (ATP) in response to VT or the delivery of high voltage defibrillation shocks in response to VF. Diagnostic information pertaining to any detected tachyarrhythmias and to the detection of any T-wave oversensing may be stored within the pacer/ICD for transmission to a bedside monitor 30, if one is provided, or for subsequent transmission to an external programmer (not shown in FIG. 4) for review by a physician or other medical professional. The physician may then prescribe any other appropriate therapies to prevent additional episodes of tachyarrhythmias. The physician may also adjust the operation of the pacer/ICD to activate, deactivate or otherwise control any therapies that are automatically applied and to adjusting the operation of the filters, if needed, to address any T-wave oversensing problems. The bedside monitor may be directly networked with a centralized computing system, such as the HouseCall™ system of St. Jude Medical, for promptly notifying the physician of any abnormal conditions, particularly any life-threatening ventricular tachyarrhythmias. Networking techniques for use with implantable medical systems are set forth, for example, in U.S. Pat. No. 6,249,705 to Snell, entitled "Distributed Network System for Use with Implantable Medical Devices."

Thus, FIG. 4 provides an overview of an implantable system for detecting tachyarrhythmias and for delivering therapy in response thereto and for detecting T-wave oversensing. Although a pacer/ICD is illustrated in FIG. 4, it should be understood that the techniques of the invention may be implemented within other implantable medical devices.

Overview of Tachyarrhythmia Detection Techniques

Figure 5:
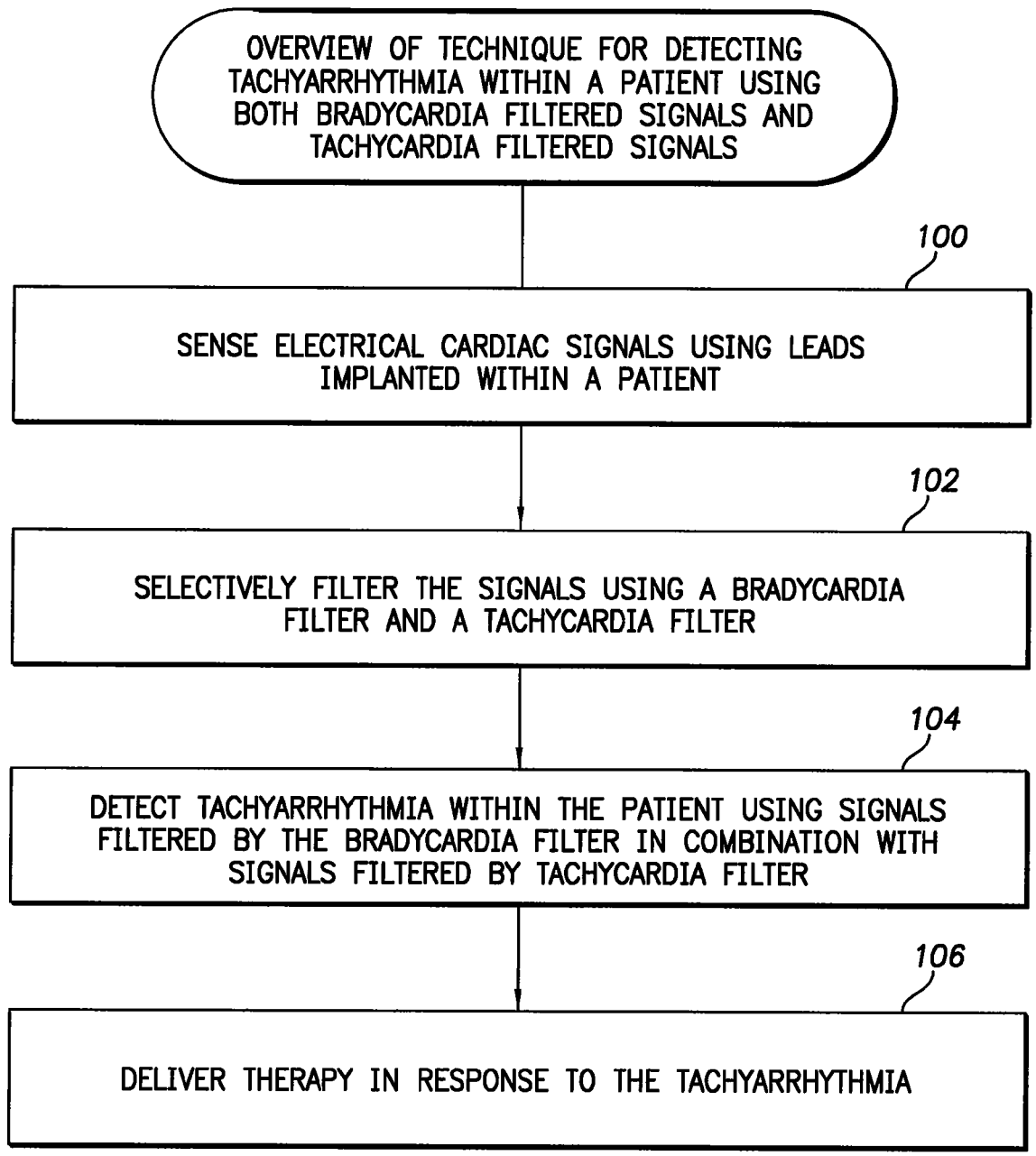
FIG. 5 provides an overview of a technique performed by the system of FIG. 4 for detecting tachyarrhythmias using the bradycardia filter in combination with the tachycardia filter and for delivering therapy in response thereto.

FIG. 5 provides an overview of the techniques of the invention for detecting tachyarrhythmias using both a narrowband bradycardia filter and a narrowband tachycardia filter. Briefly, at step 100, the pacer/ICD senses electrical cardiac signals, such as IEGM signals, using one or more leads implanted within the patient. Otherwise conventional techniques may be used for converting voltage signals sensed using the various leads into IEGM or similar signals. At step 102, the pacer/ICD selectively filters the signals using an internal narrowband bradycardia filter and an internal narrowband tachycardia filter. By a "bradycardia filter," it is meant a filter configured to pass cardiac signals appropriate for the detection of bradycardia (particularly relatively low rate R-waves) while filtering out noise and other cardiac signals, particularly T-waves. That is, the bradycardia filter is a filter operative to substantially eliminate signals having frequencies associated with ventricular repolarization events while retaining signals having frequencies associated with at least some ventricular depolarization events. The bradycardia filter is also referred to as a "first filter" herein. By a "tachycardia filter," it is meant a filter configured to pass cardiac signals appropriate for the detection of tachyarrhythmias. That is, the tachycardia filter is a filter operative to pass signals having frequencies associated with ventricular depolarization events and ventricular repolarization events. The tachycardia filter is also referred to as a "second filter" herein. Otherwise conventional bradycardia (first) and tachycardia (second) filters can be employed. In one particular example, the bradycardia filter is configured to pass signals generally in the range of 18-118 Hz. For example, the filter may be configured to have a center frequency at 50 Hz with −3 dB points set at 18 Hz and 118 Hz. In one particular example, the tachycardia filter is configured to pass signals generally in the range of 10-70 Hz. For example, the filter may be configured to have a center frequency at 30 Hz with −3 dB points set at 10 Hz and 70 Hz. As already noted, a wideband filter may additionally be employed. In one particular example, the wideband filter is configured to pass signals in the range of 1-250 Hz. For example, the filter may be configured to have a center frequency at 50 Hz with −3 dB points set at 1 Hz and 250 Hz.

As will be apparent with reference to the illustrative examples described in detail below, selective filtering of the electrical cardiac signals can include, at least: (1) filtering initial cardiac signals with just the bradycardia filter and then filtering additional cardiac signals using the tachycardia filter; (2) filtering initial cardiac signals with just the bradycardia filter and then filtering additional cardiac signals using both the bradycardia filter and the tachycardia filter operating in parallel; (3) filtering initial cardiac signals with just the tachycardia filter and then filtering additional cardiac signals using both the bradycardia filter and the tachycardia filter operating in parallel; (4) filtering initial signals using both the bradycardia filter and the tachycardia filter operating in parallel; (5) or some combination of the foregoing. Other selective filtering combinations may be appropriate as well, depending upon the implementation, including combinations including one r more wideband filters.

In some implementations, physically separate bradycardia and tachycardia filters are used. In other implementations, a single reconfigurable filter is used, which can be selectively switched by the pacer/ICD from bradycardia filtering to tachycardia filtering. The illustrative examples described herein do not specifically provide for the filtering of the same cardiac signal in series by both a bradycardia filter and a tachycardia filter (i.e. feeding the output of a bradycardia filter into a tachycardia filter, or vice versa). Although, depending upon the bandwidth characteristics of the filters, such sequential filtering of signals may potentially be appropriate or advantageous in some cases, and hence the term "selective filtering" should be construed as encompassing such as sequential filtering embodiments.

At step 104, the pacer/ICD detects tachyarrhythmia within the patient, if it is occurring, using signals filtered by the bradycardia filter in combination with signals filtered by the tachycardia filter, and, in some cases, in further combination with wideband filtered signals. Various exemplary techniques for detecting ventricular tachyarrhythmias are set forth below in the various illustrative examples. Principles of the invention may potentially be applied to the detection of atrial tachyarrhythmias as well as ventricular tachyarrhythmias, or to other atrial or ventricular arrhythmias or dysrhythmias, as well. At step 106, the pacer/ICD delivers therapy in response to the detected tachyarrhythmia, such as ATP in response to VT or defibrillation shocks in response to VF. ATP is discussed in, e.g., U.S. Pat. No. 6,907,286 to Kroll, et al., entitled "Anti-tachycardia Pacing Methods and Devices." Defibrillation therapy is discussed in, e.g., U.S. Pat. No. 6,772,007 to Kroll, entitled "System and Method of Generating a Low-Pain Multi-Step Defibrillation Waveform for Use in an Implantable Cardioverter/Defibrillator (ICD)."

Note that, whereas the techniques of FIG. 5 are preferably employed in "real time" based on IEGM signals as they are sensed, the techniques can alternatively be employed based on previously recorded signals. For example, IEGM data may be collected over time then analyzed later to detect episodes of arrhythmias that may have already occurred for the purpose of generate appropriate diagnostic data for physician review. Such delayed analysis techniques can be performed either using the implanted device itself or using an external data processing device based on data transmitted from the implanted device. Real time detection is preferred as it allows arrhythmias to be promptly detected so that appropriate therapy can be promptly delivered. In the examples below, ventricular tachyarrhythmias are detected though, as noted, principles of the invention are potentially applicable to the detection of atrial tachyarrhythmias as well.

First Exemplary Ventricular Tachyarrhythmia Detection Technique

Figure 6:
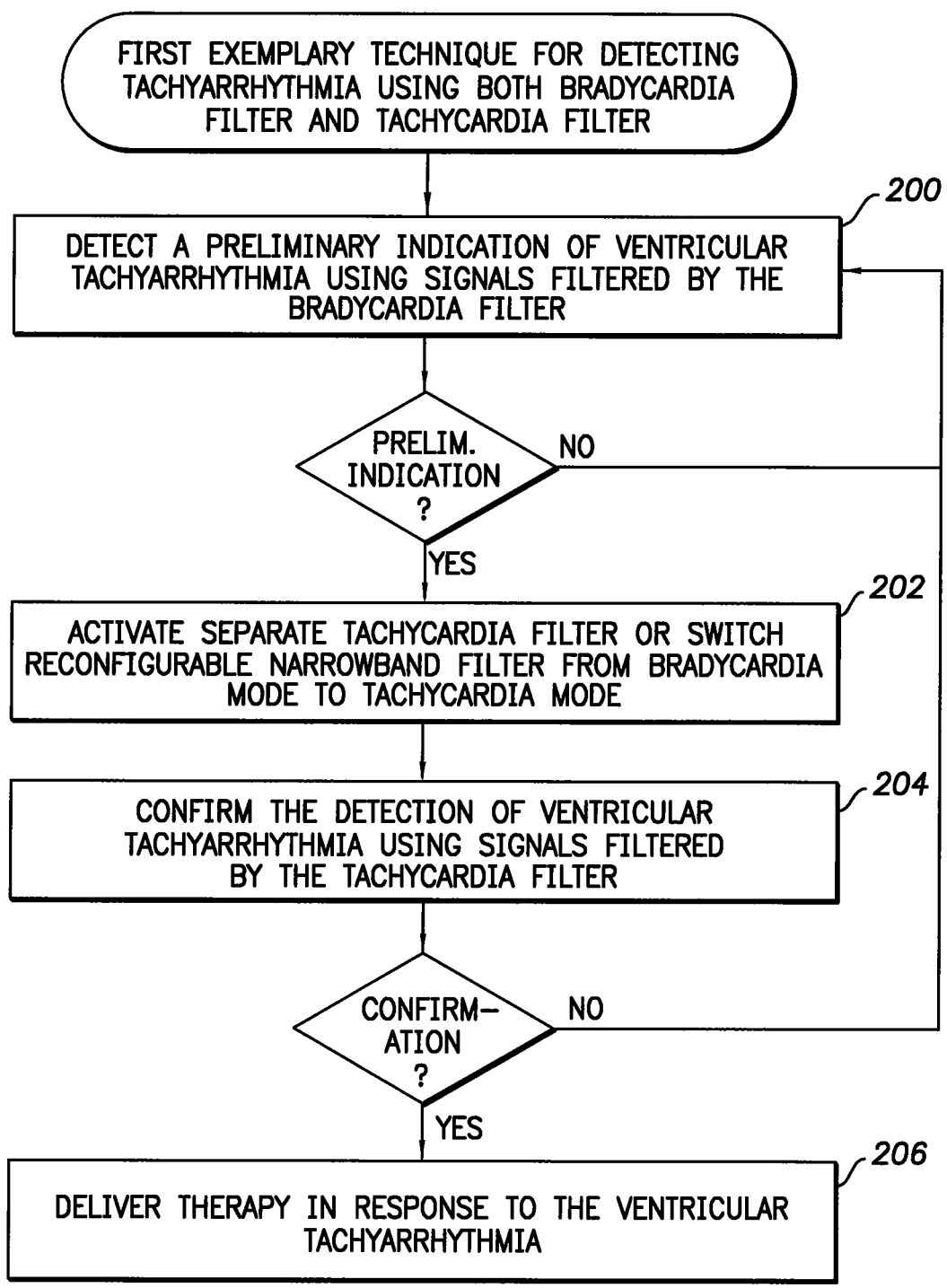
FIG. 6 illustrates a first illustrative example of the tachyarrhythmia detection technique of FIG. 5, wherein the bradycardia filter is used to provide a preliminary indication of tachyarrhythmia, which is then confirmed using the tachycardia filter.
Figure 7:
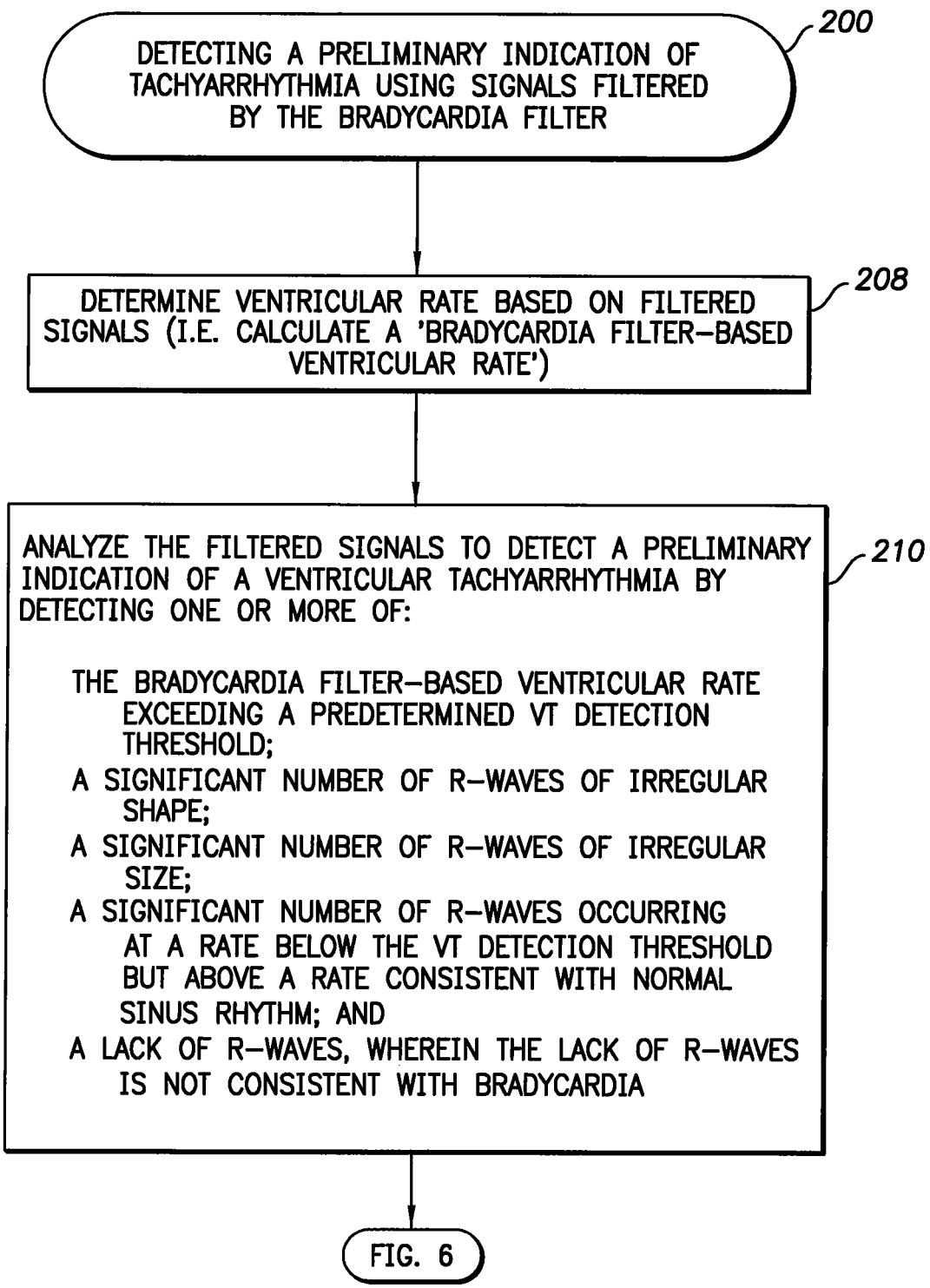
FIG. 7 particularly illustrates techniques for detecting a preliminary indication of tachyarrhythmia using the bradycardia filter for use with the embodiment of FIG. 6.
Figure 8:
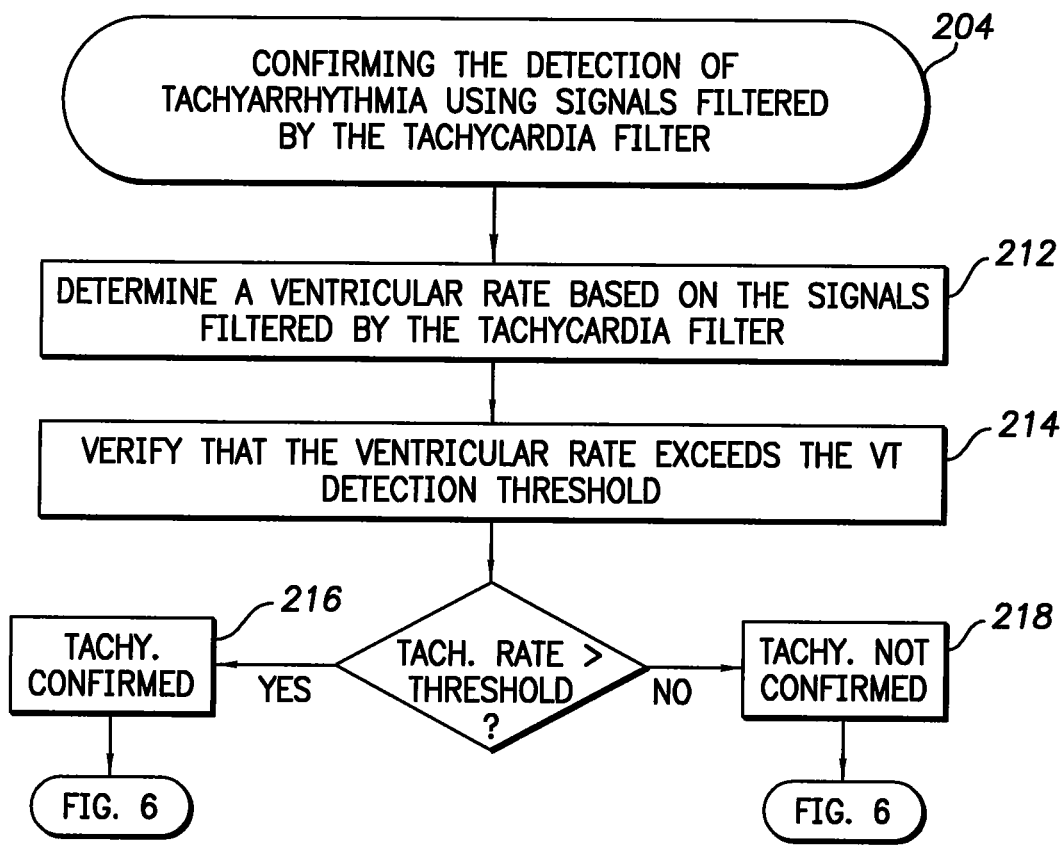
FIG. 8 particularly illustrates techniques for confirming the detection of tachyarrhythmia using the tachycardia filter also for use with the embodiment of FIG. 6.

FIG. 6 illustrates a first exemplary technique, wherein the bradycardia filter is used to provide a preliminary indication of ventricular tachyarrhythmia, which is then confirmed using the tachycardia filter. At step 200, the pacer/ICD detects a preliminary indication of ventricular tachyarrhythmia using signals filtered by the bradycardia filter. That is, ventricular channel electrical cardiac signals sensed, e.g., between an RV tip electrode and the device housing or between the RV tip electrode and an LV tip electrode, are filtered by the bradycardia filter and then analyzed to determine whether there is a significant likelihood that a ventricular tachycardia is occurring. Specific techniques for use at step 200 to detect the preliminary indication are illustrated in FIG. 7 and will be discussed below. If a preliminary indication is detected, then, at step 202, pacer/ICD activates a tachycardia filter or, if a reconfigurable filter is provided, the pacer/ICD switches the reconfigurable filter from a bradycardia-filtering mode to a tachycardia-filtering mode. At step 204, the pacer/ICD then confirms the detection of the ventricular tachyarrhythmia using signals filtered by the tachycardia filter. That is, additional ventricular channel signals are filtered by the tachycardia filter and then analyzed to determine whether the ventricular tachycardia is, indeed, occurring. Specific techniques for use in confirming ventricular tachyarrhythmia at step 204 are illustrated in FIG. 8 and will be discussed below. Assuming the arrhythmia is confirmed then, at step 206, appropriate therapy is delivered.

Although not shown, the pacer/ICD, at step 206, preferably determines the particular ventricular tachyarrhythmia, e.g., VT or VF and then delivers therapy appropriate to the arrhythmia. Otherwise conventional techniques for distinguishing among different types of ventricular tachyarrhythmias may be employed. For example, the ventricular rate can be compared against separate VT and VF thresholds. If the rate exceeds a higher VF threshold (set, e.g., to 220 beats per minute (bpm)), then VF is presumed and defibrillation shocks are delivered. If the rate only exceeds the lower VT threshold (set, e.g., to 180 bpm), then VT is presumed and ATP is delivered. More sophisticated discrimination techniques may be employed as well. See, for example, U.S. Pat. No. 5,404,880 to Throne, entitled "Scatter Diagram Analysis System and Method for Discriminating Ventricular Tachyarrhythmias." Note that, up on detection of the preliminary indication of a ventricular tachyarrhythmia at step 200, defibrillation capacitors may be pre-charged so that, if VF is subsequently detected, defibrillation shocks can be more promptly delivered.

FIG. 7 illustrates techniques for detecting a preliminary indication of ventricular tachyarrhythmias using signals filtered by the bradycardia filter. At step 208, the pacer/ICD determines a ventricular rate based on the ventricular channel signals filtered by the bradycardia filter, i.e. the device calculates a "bradycardia filter-based ventricular rate." At step 210, the pacer/ICD analyzes the filtered signals to detect a preliminary indication of ventricular tachyarrhythmia by detecting one or more of:

(a) the bradycardia filter-based ventricular rate exceeding a predetermined VT detection threshold;

(b) a significant number of R-waves of irregular shape;

(c) a significant number of R-waves of irregular size;

(d) a significant number of R-waves occurring at a rate below the VT detection threshold but above a rate consistent with normal sinus rhythm; and/or (e) a lack of R-waves, wherein the lack of R-waves is not consistent with bradycardia.

Now considering these conditions individually, insofar as (a) is concerned, the typical bradycardia filter (assuming its sensitivity and other parameters are set properly) will accurately detect "well formed" R-waves occurring, even those occurring at VT rates. By "well formed," it is meant that the R-waves have relatively normal morphology, i.e. they are not significantly distorted and are not fused with other ventricular events. (Irregular R-waves may or may not be detected, depending upon their shape and magnitude.) Accordingly, the bradycardia filter-based ventricular rate can be compared against the VT threshold (e.g. 180 bpm) to detect the preliminary indication of ventricular tachyarrhythmia. The resulting indication of ventricular tachyarrhythmia is preliminary only and, as noted, confirmation is performed using the tachycardia filter before any therapy is actually delivered. Note, also, that the typical bradycardia filter will not detect R-waves associated with VF, as such events are usually too fast or are poorly formed.

Insofar as (b) is concerned, a preliminary indication of a ventricular tachyarrhythmia is generated if there are a significant number of R-waves of irregular shape. In this regard, although the bradycardia filter will not accurately detect all non-"well formed" R-waves, it may nevertheless detect some, and the presence of a significant number of irregular shape R-waves is an indication of a possible tachyarrhythmia. Hence, a counter is used to count the number of such irregularly shaped R-waves and, if the count exceeds some predetermined threshold (e.g. X out Y R-waves have irregular shapes, where X and Y are programmable values), then the preliminary indication of a ventricular tachyarrhythmia is generated. Otherwise conventional morphological analysis techniques may be used to examine the R-waves to distinguish "well formed" R-waves from irregular R-waves.

Insofar as (c) is concerned, a preliminary indication of a ventricular tachyarrhythmia is generated if there are a significant number of R-waves of irregular size. In this regard, the presence of a significant number of R-waves that are either much larger or much smaller than the average is an indication of a possible tachyarrhythmia. Hence, a counter is used to count the number of such irregularly sized R-waves and, if the count exceeds some predetermined threshold (e.g. X out Y R-waves have irregularly sizes), then the preliminary indication of a ventricular tachyarrhythmia is generated. Otherwise conventional amplitude measurement techniques may be used to identify irregularly sized R-waves.

Insofar as (d) is concerned, the preliminary indication is generated if there are a significant number of R-waves occurring at a rate below the VT detection threshold but above a rate consistent with normal sinus rhythm. To account for the possibility that some R-waves during VT might not be detected by the bradycardia filter because they are not well formed or because the filter parameters are not set properly to detect high rate R-waves, it is appropriate to define a somewhat lower "ventricular tachyarrhythmia preliminary detection threshold", i.e. a threshold somewhat lower than the 180 bpm VT threshold. In one example, the lower threshold is set to, e.g., 160 bpm. Accordingly, a preliminary indication of ventricular tachyarrhythmia may be generated whenever a significant number of R-waves (i.e. X out of Y, where X and Y are programmable) exceed the "ventricular tachyarrhythmia preliminary detection threshold."

Insofar as (e) is concerned, a preliminary indication of a ventricular tachyarrhythmia is generated if there is a significant lack of R-waves, wherein the lack of R-waves is not consistent with bradycardia. As noted, during VF, R-waves are not typically detected by the bradycardia filter. Accordingly, a lack of R-waves may be indicative of bradycardia or VF. To determine whether the lack of R-waves is not consistent with bradycardia, the pacer/ICD may, for example, examine the bradycardia-filtered rate just prior to the period when R-waves no longer appear. If the rate was rapidly increasing toward the VT threshold, such would not be consistent with bradycardia, and the preliminary indication of ventricular tachyarrhythmia would be generated. If the rate was dropping from a normal sinus rhythm rate, such would be consistent with bradycardia, and so no indication of ventricular tachyarrhythmia would be generated. (Instead, an indication of bradycardia would be generated and appropriate bradycardia therapy delivered.)

Hence, FIG. 7 illustrates some techniques for rendering a preliminary determination of ventricular tachyarrhythmia based on signals filtered with a bradycardia filter. Other techniques may be appropriate as well. Multiple techniques may be employed in combination.

FIG. 8 illustrates an exemplary technique for confirming the detection of a ventricular tachyarrhythmia using signals filtered by the tachycardia filter. At step 212, the pacer/ICD determines a ventricular rate based on the signals filtered by the tachycardia filter, i.e. the pacer/ICD calculates a "tachycardia filter-based ventricular rate." At step, 214, the pacer/ICD verifies that the ventricular rate exceeds, at least, the VT detection threshold. If so, then the ventricular tachyarrhythmia is confirmed at step 216. Otherwise, it is disconfirmed, at step 218. As already explained, before any therapy is actually delivered, the pacer/ICD distinguishes between VT and VF, typically be employing a still higher VF threshold. FIG. 8 merely illustrates one exemplary technique for confirming ventricular tachyarrhythmia based using signals filtered by the tachycardia filter. Other techniques may additionally or alternatively be employed.

Second Exemplary Ventricular Tachyarrhythmia Detection Technique

Figure 9:
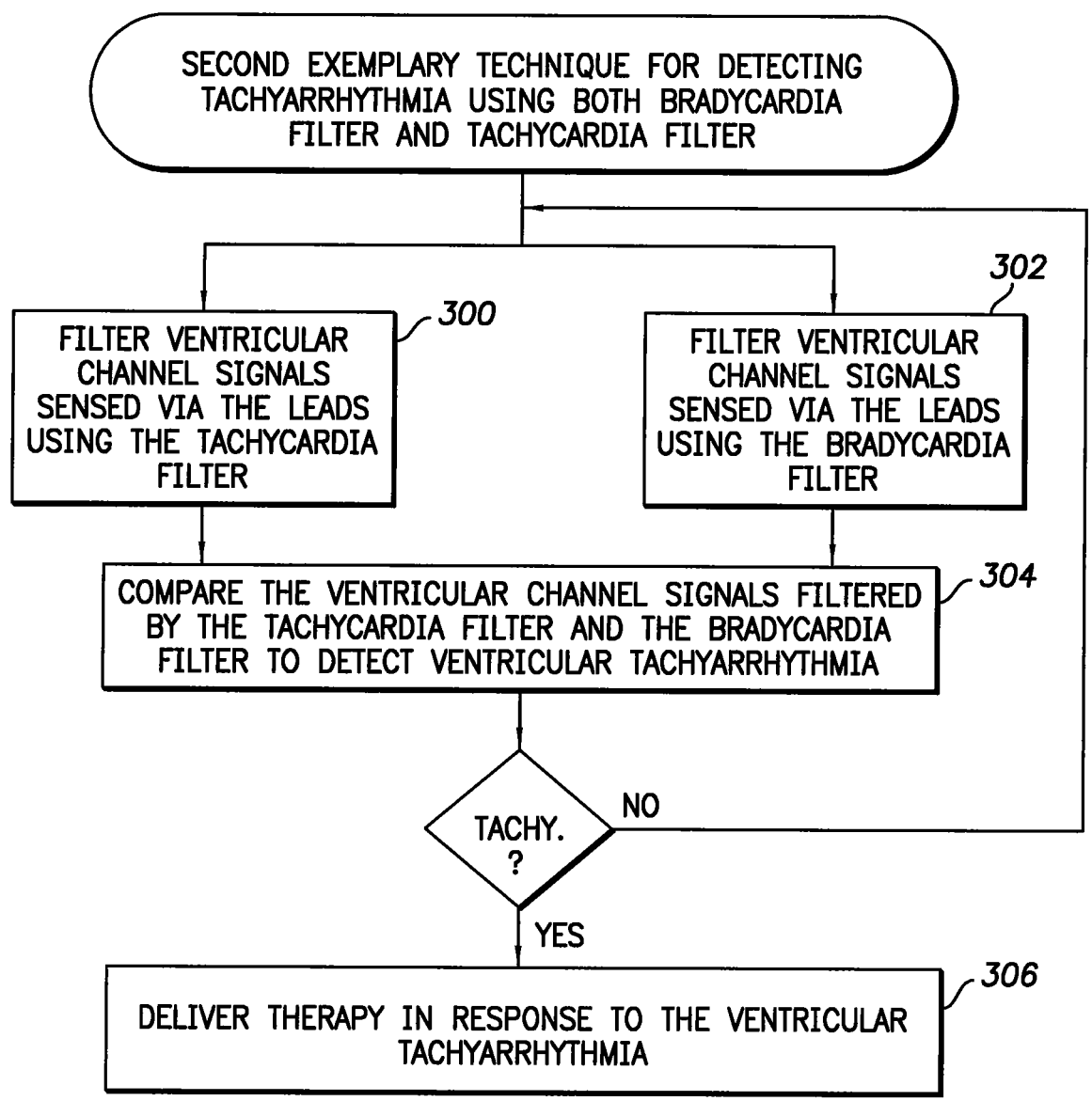
FIG. 9 illustrates a second illustrative example of the tachyarrhythmia detection technique of FIG. 5, wherein signals filtered by the bradycardia filter are compared with signals filtered by the tachycardia filter to detect tachyarrhythmia.

FIG. 9 illustrates the second exemplary technique, wherein signals filtered by the bradycardia filter are compared with signals filtered by the tachycardia filter to detect tachyarrhythmia, i.e. the bradycardia and the tachycardia filter operate in parallel. Since the filters operate in parallel, a reconfigurable filter of the type described above is not used. Rather, separate bradycardia and tachycardia filters are employed. At step 300, the pacer/ICD filters ventricular channel signals sensed via the leads using the tachycardia filter while, at step 302, also filtering ventricular channel signals sensed via the leads using the bradycardia filter. At step 304, the pacer/ICD compares the ventricular 0channel signals filtered by the tachycardia filter and the bradycardia filter to detect ventricular tachyarrhythmia. Assuming a ventricular arrhythmia is detected then, at step 306, appropriate therapy is delivered.

Figure 10:
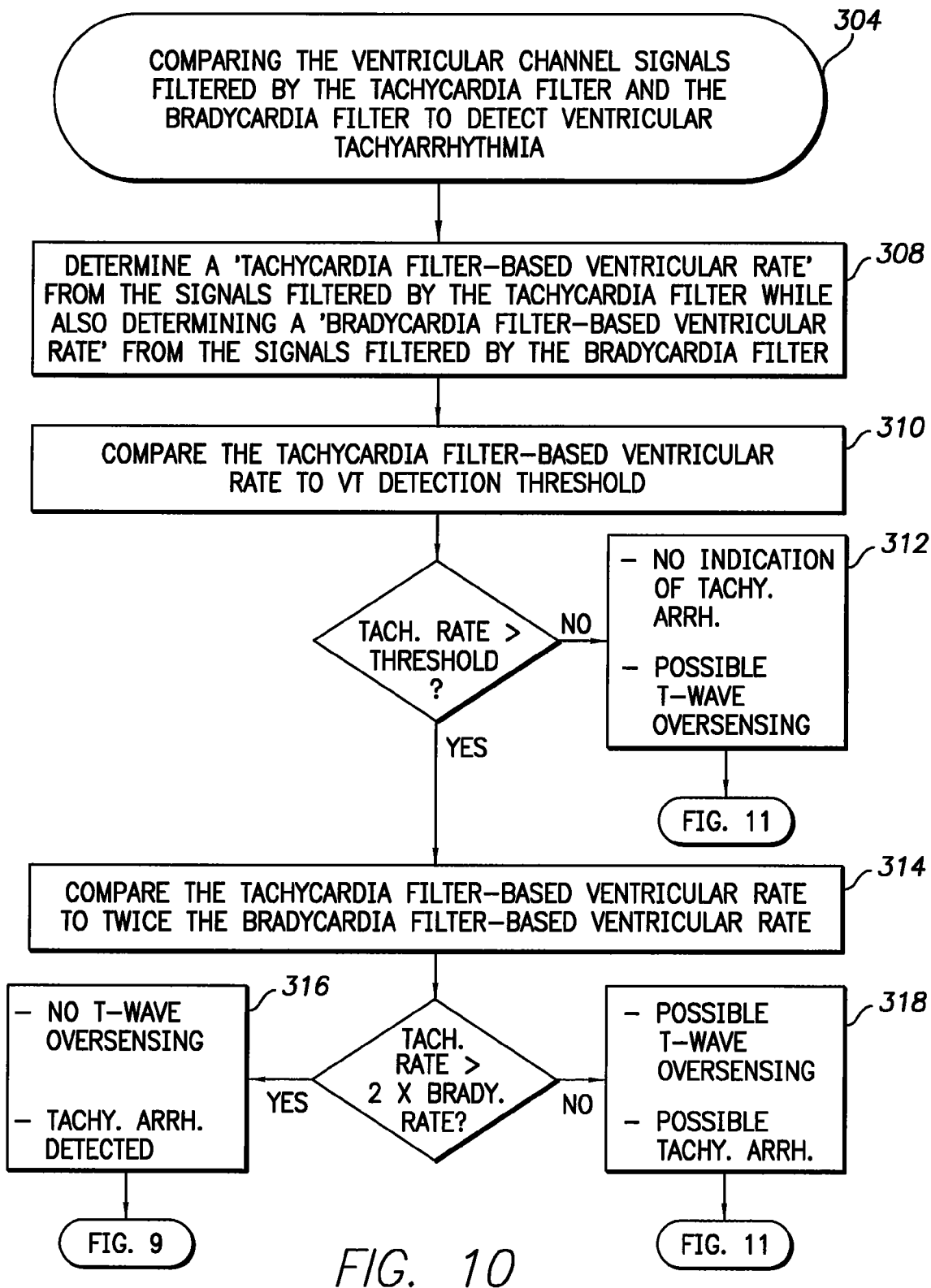
FIG. 10 particularly illustrates techniques for comparing the signals filtered by the bradycardia filter with the signals filtered by the tachycardia filter for use with the embodiment of FIG. 9.

FIG. 10 illustrates techniques for detecting ventricular tachyarrhythmia based on a comparison between bradycardia-filtered signals and tachycardia-filter signals for use at step 304 of FIG. 9. At step 308, the pacer/ICD determines a "tachycardia filter-based ventricular rate" from the signals filtered by the tachycardia filter while also determining a "bradycardia filter-based ventricular rate" from the signals filtered by the bradycardia filter. At step 310, the pacer/ICD compares the tachycardia filter-based ventricular rate to VT detection threshold. If the tachycardia filter-based rate does not exceed the threshold, then there is no indication of ventricular tachyarrhythmia, step 312. However, T-wave oversensing may be occurring and so further processing is performed, which will be described with reference to FIG. 11. If, however, the tachycardia filter-based rate exceeds the VT threshold, then, at step 314, the pacer/ICD compares the tachycardia filter-based ventricular rate to twice the bradycardia filter-based ventricular rate. If the tachycardia filter-based ventricular rate is greater than twice the bradycardia filter-based ventricular rate, then ventricular tachyarrhythmia is thereby detected without further processing (i.e. T-wave oversensing is not implicated.) If, however, the tachycardia filter-based ventricular rate is not greater than twice the bradycardia filter-based ventricular rate, then a ventricular tachyarrhythmia might be occurring or the high rate might be due to T-wave oversensing and so further processing is required, which will also be described with reference to FIG. 11.

In other words, if the tachycardia filter-based ventricular rate is greater than the VT threshold and if the tachycardia filter-based ventricular rate is also greater than twice the bradycardia filter-based ventricular rate, a tachyarrhythmia is immediately detected (block 316) without the need for further processing. In the regard, tachycardia is almost certainly occurring, since T-wave oversensing, by itself, would not produce such a result. T-wave oversensing results in, at most, a tachycardia-filtered rate that is twice the bradycardia-filtered rate (i.e. each T-wave is misidentified as an R-wave.) If, instead, the tachycardia filter-based ventricular rate is greater than the VT threshold but not greater than twice the bradycardia filter-based ventricular rate (block 318), then additional confirmation procedures are needed to verify the tachyarrhythmia before therapy is delivered.

Accordingly, at step 320 of FIG. 11, the pacer/ICD initiates additional VT/VF confirmation procedures, i.e. detection procedures not based solely on the tachycardia rate and the VT and VF thresholds. Techniques described below with reference to FIGS. 13-19, wherein the pacer/ICD distinguishes between true and false R-waves, may be appropriate for use at step 320. Also, morphology-based detection VT/VF techniques may be used. See, also, U.S. Pat. No. 5,623,936 to McClure, entitled "Implantable Medical Device having Means for Discriminating between True R-Waves and Ventricular Fibrillation." If VT/VF is confirmed by the alternative techniques, then processing returns to FIG. 9 and therapy is promptly delivered. Otherwise, the high tachycardia rate was deemed to be due to T-wave oversensing and sensitivity of the tachycardia filter is adjusted at step 322 in an attempt to eliminate or reduce oversensing, such as by decreasing the sensitivity of the tachycardia filter.

If, at step 312 of FIG. 10, the tachycardia filter-based ventricular rate was not greater than the VT threshold, then there is no indication of an arrhythmia, but T-wave oversensing may be occurring and so further processing is warranted. Accordingly, at step 324 of FIG. 11, the pacer/ICD compares the tachycardia filter-based ventricular rate to twice the bradycardia filter-based ventricular rate and if it is found to be about equal to twice the bradycardia filter-based ventricular rate, T-wave oversensing is thereby detected, step 326, and the sensitivity of the tachycardia filter is adjusted at step 328. In this regard, if the ventricular rate derived from the tachycardia filter is about equal to twice the ventricular rate derived bradycardia filter, but below the VT threshold, the tachycardia filter rate is likely due to T-wave oversensing, i.e. each T-wave is being misidentified as an R-wave, yielding a rate double that of the bradycardia filter. Otherwise, if the tachycardia-filtered rate is not about equal to twice the bradycardia rate, then no T-wave oversensing is detected, step 328, and processing merely returns to FIG. 9.

The logic of FIGS. 9-11 is summarized in Table I, above. As further indicated in the table, if the rate derived from the tachycardia filter is well below the VT threshold and is also about equal to the rate derived from the bradycardia filter, then normal sinus rhythm is occurring without T-wave oversensing and so no action need be taken.

Third Exemplary Ventricular Tachyarrhythmia Detection Technique

Figure 12:
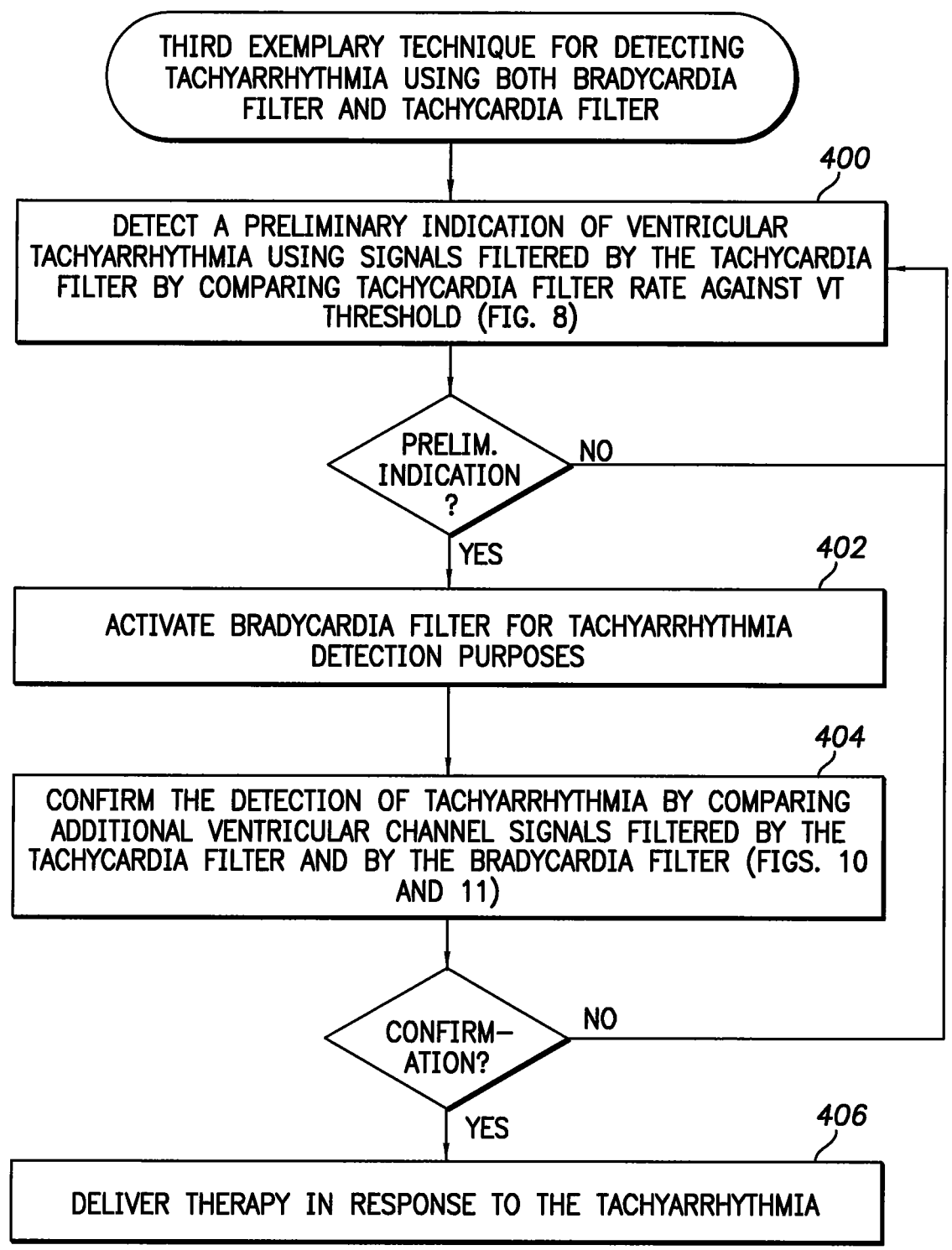
FIG. 12 illustrates a third illustrative example of the tachyarrhythmia detection technique of FIG. 5, wherein a preliminary indication of tachyarrhythmia is made using the tachycardia filter and then additional signals filtered by the bradycardia filter are compared with additional signals filtered by the tachycardia filter to confirm detection of the tachyarrhythmia.

FIG. 12 illustrates the third exemplary technique, wherein a preliminary indication of tachyarrhythmia is made using the tachycardia filter and then additional signals filtered by the bradycardia filter are compared with additional signals filtered by the tachycardia filter to confirm detection of the tachyarrhythmia. At step 400, the pacer/ICD detects a preliminary indication of ventricular tachyarrhythmia using signals filtered by the tachycardia filter by comparing tachycardia filter rate against VT threshold. See, for example, FIG. 8. If a preliminary indication is detected, then the pacer/ICD proceeds to confirm the tachyarrhythmia by using the bradycardia filter in combination with the tachycardia filter. Accordingly, at step 402, the pacer/ICD activates the bradycardia filter for tachyarrhythmia detection purposes. In this regard, the bradycardia filter may already be operating to detect bradycardia, in which case the pacer/ICD just begins routing output signals from the bradycardia filter to the tachyarrhythmia detection system. If not already active, the pacer/ICD activates the bradycardia filter to beginning filtering ventricular channel signals. In any case, at step 404, the pace/ICD confirms the detection of tachyarrhythmia by comparing additional ventricular channel signals filtered by the tachycardia filter and by the bradycardia filter. The techniques just described with reference to FIGS. 10 and 11 may be used. Assuming the tachyarrhythmia is confirmed then, at step 406, appropriate therapy is delivered.

Hence, the embodiment of FIG. 12 is similar to that of FIGS. 9-11, described above, but with FIG. 12 the tachycardia filter is initially used to detect a preliminary indication of tachyarrhythmia before any bradycardia-filtered signals are compared against tachycardia-filtered signals. The preliminary indication may be used, e.g., to trigger charging of defibrillation capacitors in the case that a defibrillation shock is ultimately required.

Fourth Exemplary Ventricular Tachyarrhythmia Detection Technique

Figure 13:
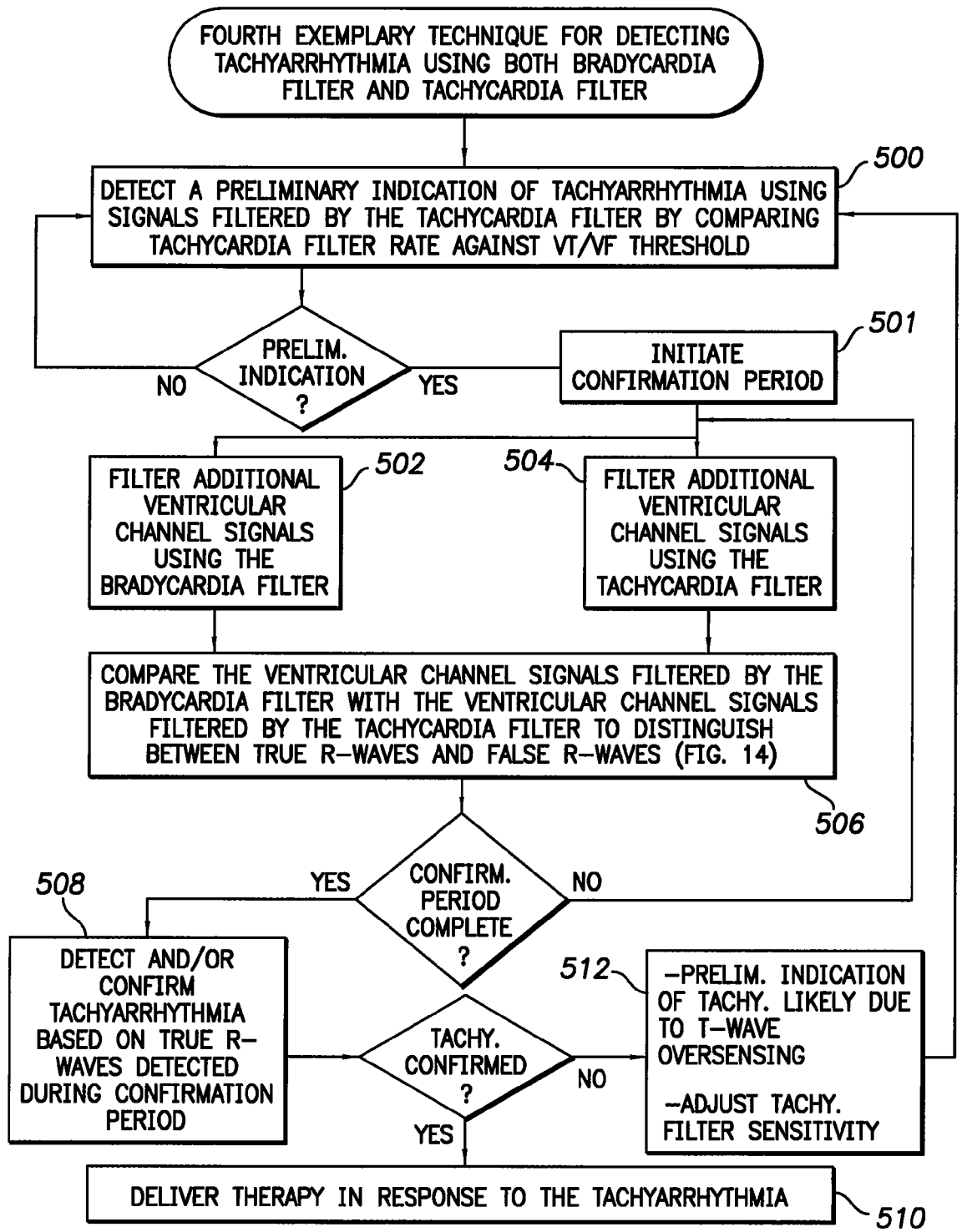
FIG. 13 illustrates a fourth illustrative example of the tachyarrhythmia detection technique of FIG. 5, wherein a preliminary indication of tachyarrhythmia is made using the tachycardia filter and then additional signals filtered by the bradycardia filter are compared with additional signals filtered by the tachycardia filter to identify true R-waves (as opposed to oversensed T-waves) so as to permit detection of tachyarrhythmia based only on true R-waves.

FIG. 13 summarizes the fourth exemplary technique, wherein a preliminary indication of tachyarrhythmia is made using the tachycardia filter and then additional signals filtered by the bradycardia filter are compared with additional signals filtered by the tachycardia filter to identify true R-waves (as opposed to oversensed T-waves) so as to permit detection of tachyarrhythmia based only on true R-waves. At step 500, the pacer/ICD detects a preliminary indication of ventricular tachyarrhythmia using signals filtered by the tachycardia filter by comparing tachycardia filter rate against VT threshold. See, for example, FIG. 8. If a preliminary indication is detected, then the pacer/ICD initiates a confirmation period or confirmation interval during which the device seeks to confirm the tachyarrhythmia before therapy is delivered. The confirmation period may extend, e.g., for 100 ventricular event cycles following the preliminary detection at step 500. Alternatively, the confirmation period may be specified as a predetermined number of seconds, such as 30 seconds, or as the lesser of a predetermined number of ventricular event cycles or a predetermined number of seconds. In any case, during the confirmation period, steps 502 and 504 are performed wherein the pacer/ICD filters additional ventricular channel signals, in parallel, using both the bradycardia filter and the tachycardia filter.

At step 506, the pacer/ICD compares the ventricular channel signals filtered by the bradycardia filter with the ventricular channel signals filtered by the tachycardia filter to distinguish between true R-waves and false R-waves (i.e. oversensing T-waves). Techniques set forth in FIG. 14, described below, may be employed. Following completion of the confirmation period, the pacer/ICD then detects and/or confirms the ventricular tachyarrhythmia, at step 508, based on the true R-waves, and only the true R-waves, detected during the confirmation period. That is, oversensed T-waves occurring during the confirmation period are ignored for the purposes of confirmation of the ventricular tachyarrhythmia. In one example, the pacer/ICD calculates a "true ventricular rate" using only the true R-waves and compares the true ventricular rate against the VT threshold to confirm the tachyarrhythmia. Assuming the tachyarrhythmia is confirmed then, at step 510, appropriate therapy is delivered. If not, then the preliminary indication of tachyarrhythmia made at step 500 was likely due to oversensed T-waves and so the device, at step 512, adjusts the sensitivity of the tachycardia filter in an attempt to reduce or eliminate such oversensing.

Figure 14:
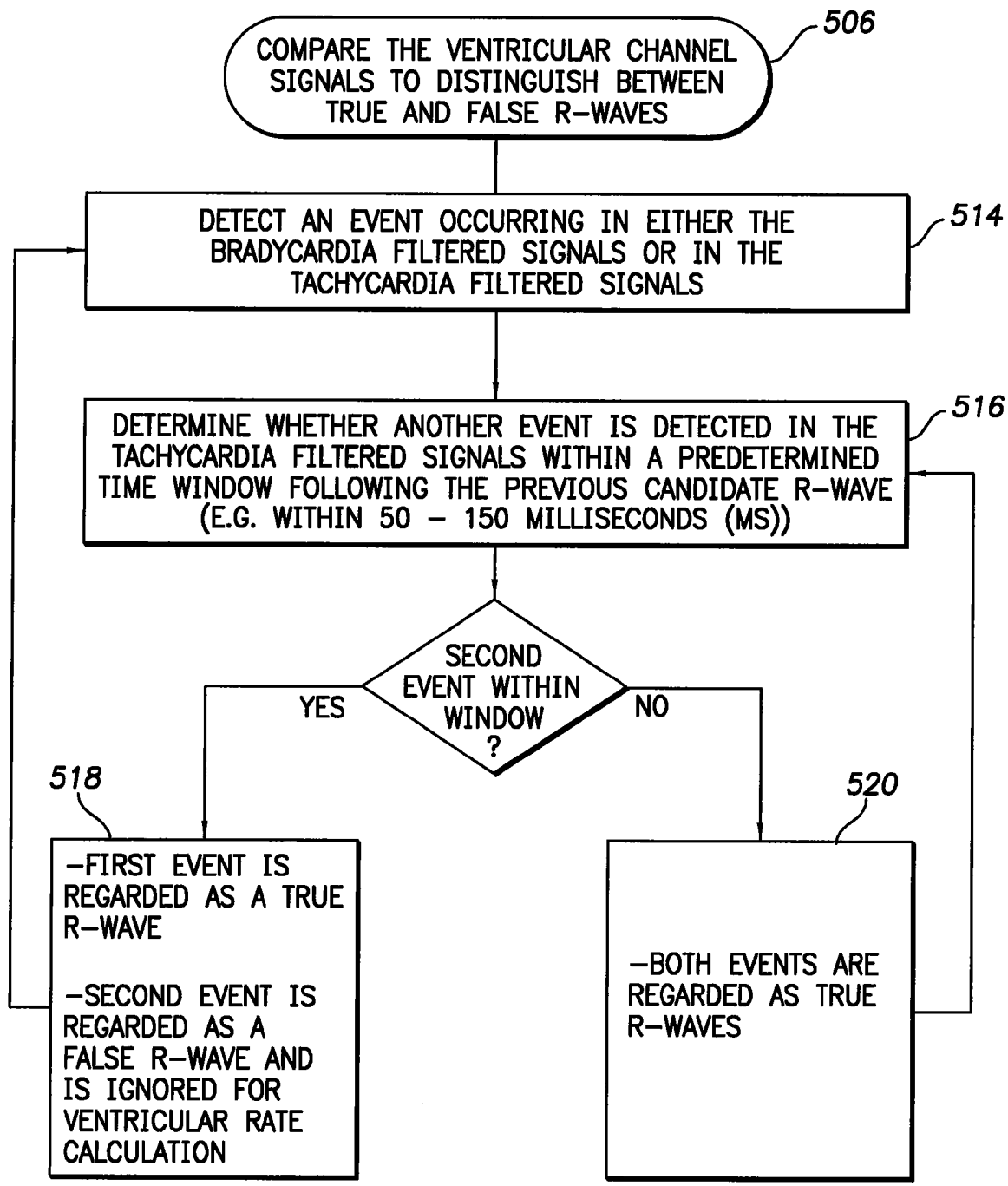
FIG. 14 particularly illustrates techniques for distinguishing true and false R-waves for use with the embodiment of FIG. 13.

Turning now to FIG. 14, an exemplary technique for distinguishing true and false R-waves will be described for use at step 506 of FIG. 13. At step 514, the pacer/ICD detects a first event in either the bradycardia-filtered signals or in the tachycardia-filtered signals. In some cases, that event may appear first in the bradycardia-filtered signal. In other cases, it may appear first in the tachycardia-filtered signal. In still other cases, the event may appear substantially simultaneously in both signals. Next, at step 516, the pacer/ICD determines whether another (i.e. a second) event is detected in the tachycardia filtered signals within a predetermined time window following the first event (e.g. within 50-150 milliseconds (ms)). If a second event is detected in the tachycardia-filtered signals within the window, then the first event is deemed to be a true R-wave whereas the second event is deemed to be an oversensed T-wave and is ignored for the purposes of ventricular rate calculation. In other words, if a pair of consecutive events is separated by less than the window interval, then the second of the pair of events is regarded as being an oversensed T-wave and is ignored for the purposes of the ventricular rate calculation. The first event of the pair, however, is counted. Processing then returns to step 514, wherein the pacer/ICD waits to detect another event in either the bradycardia and/or the tachycardia-filtered signals.

If, however, the second event is not detected in the tachycardia-filtered signals until after the end of the time window, then both the first and second events of the pair of events are deemed to be true R-waves. In other words, if a pair of consecutive events is separated by more than the window interval, then the two events are both regarded as being true R-waves. Processing then returns to step 516, wherein the pacer/ICD waits to detect another event in the tachycardia-filtered signals. Note that, following step 518, processing returns to step 514; whereas, following step 520, processing returns to step 516. In this regard, following step 518, since the second event of the pair of events was rejected as being a T-wave, the next event to be detected on either the bradycardia or tachycardia channels will likely be the next true R-wave and is hence should be regarded as the first event of the next pair of events. Thus, further processing at step 514 is appropriate. However, following step 520, since the second event of the pair of events was deemed to be a true R-wave, that second event can be regarded as the first event of the next pair of events, and hence further processing at step 516 is appropriate.

Figure 15:
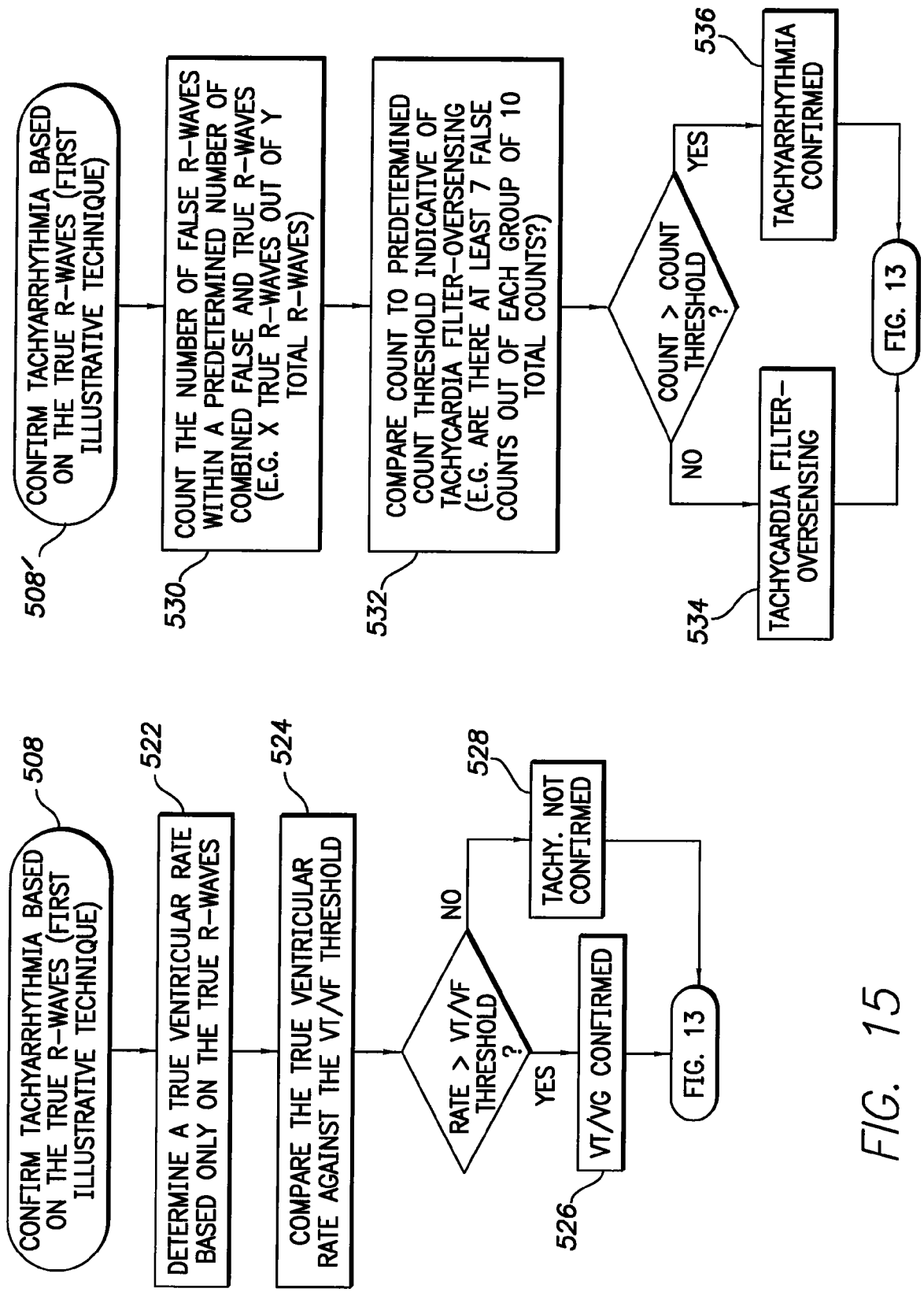
FIG. 15 particularly illustrates techniques for confirming tachyarrhythmias based on the true R-waves for use with the embodiment of FIG. 13.

Turning now to FIG. 15, exemplary techniques for confirming tachyarrhythmia based on true R-waves will be described for use at step 508 of FIG. 13. At step 522, a first illustrative technique begins, wherein the pacer/ICD determines a true ventricular rate based only on the true R-waves. Then, at step 524, the pacer/ICD compares the true ventricular rate against the VT threshold and, if the rate exceeds the threshold, tachyarrhythmia is confirmed, at step 526. Otherwise, tachyarrhythmia is disconfirmed, at step 528. Thus, the first illustrative confirmation technique uses only the true R-waves. The second illustrative technique 509' of FIG. 15 instead examines both true and false R-waves. That is, beginning at step 530, the pacer/ICD counts the number of false R-waves within a predetermined number of combined false and true R-waves (e.g. X true R-waves out of Y total R-waves.) Then, at step 532, the pacer/ICD compares the count to a predetermined count threshold indicative of tachycardia filter oversensing (e.g. are there at least seven false counts out of each group of 10 total counts?) If so, then the tachyarrhythmia is disconfirmed, at step 534. That is, the majority of R-waves are false R-waves and hence significant T-wave oversensing is occurring. As such, the high ventricular rate initially detected at step 500 of FIG. 13 was likely due to T-wave oversensing and was not indicative of a true ventricular tachyarrhythmia. If however, the count of false R-waves does not exceed the count threshold, the tachyarrhythmia is confirmed, at step 536. That is, the majority of R-waves are true R-waves and so the high ventricular rate initially detected at step 500 of FIG. 13 is indicative of a true ventricular tachyarrhythmia.

Hence, the embodiment of FIGS. 13-15 uses the tachycardia filter to detect a preliminary indication of tachyarrhythmia then compares tachycardia and bradycardia filtered signals to distinguish true R-waves from false R-waves and to then confirm or disconfirm the tachyarrhythmia based on the true R-waves.

Fifth Exemplary Ventricular Tachyarrhythmia Detection Technique

Figure 16:
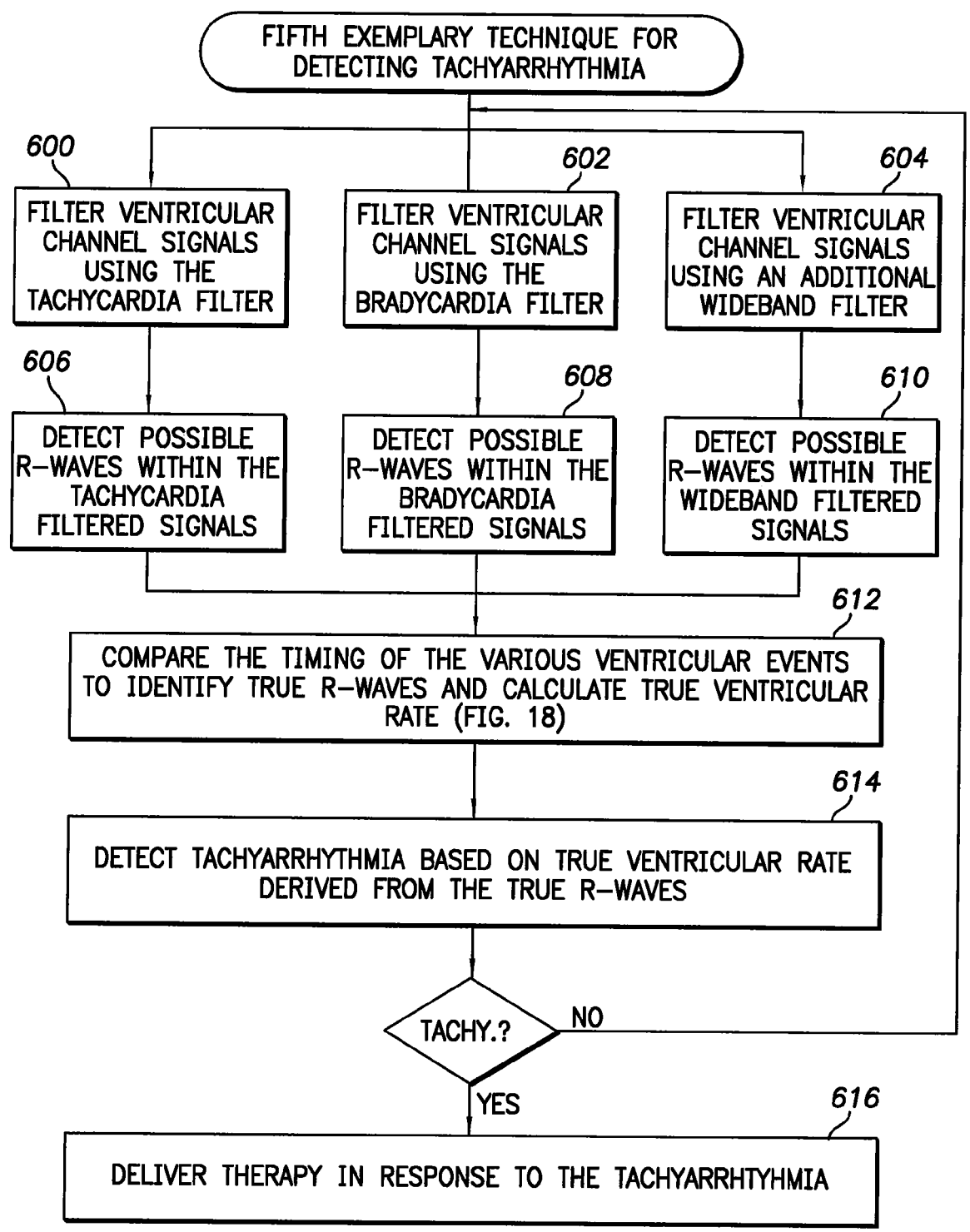
FIG. 16 illustrates a fifth illustrative example of the tachyarrhythmia detection technique of FIG. 5, wherein signals filtered by a bradycardia filter, a tachycardia filter and a wideband filter are compared to identify true R-waves so as to permit detection of tachyarrhythmia based only on true R-waves.
Figure 18:
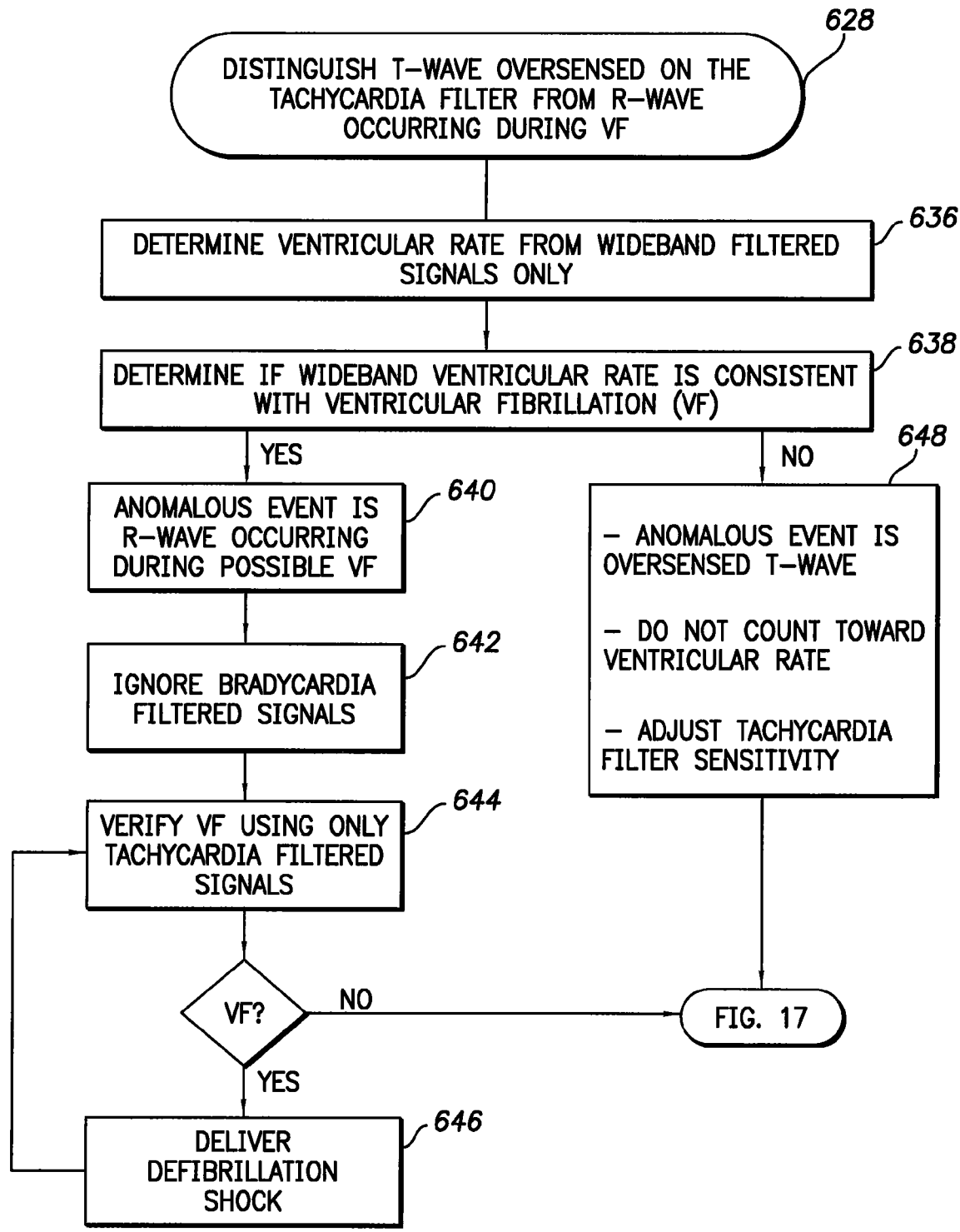
FIG. 18 particularly illustrates techniques for distinguishing T-waves oversensed on the tachycardia filter from R-waves occurring during VF for use with the techniques of FIG. 17.

FIG. 16 summarizes the fifth exemplary technique, wherein signals filtered by the bradycardia filter, the tachycardia filter and a wideband filter are compared to identify true R-waves so as to permit detection of tachyarrhythmia based only on true R-waves. Thus, with the technique of FIG. 16 a wideband filter is also employed. Beginning at steps 600, 602 and 604, the pacer/ICD simultaneously filters ventricular channel cardiac signals using the tachycardia filter, the bradycardia filter and the wideband filter, respectively. Then, at steps 606, 608 and 610, the pacer/ICD detects possible R-waves within the signals filtered by the tachycardia filter, the bradycardia filter and the wideband filter, respectively. At step 612, the pacer/ICD compares the timing of the various ventricular events to identify true R-waves and to calculate true ventricular rate. Techniques for use at step 612 are illustrated in FIG. 18, to be discussed below. Then, at step 614, the pacer/ICD detects tachyarrhythmia based on true ventricular rate derived from the true R-waves and, at step 616, delivers appropriate therapy.

Figure 17:
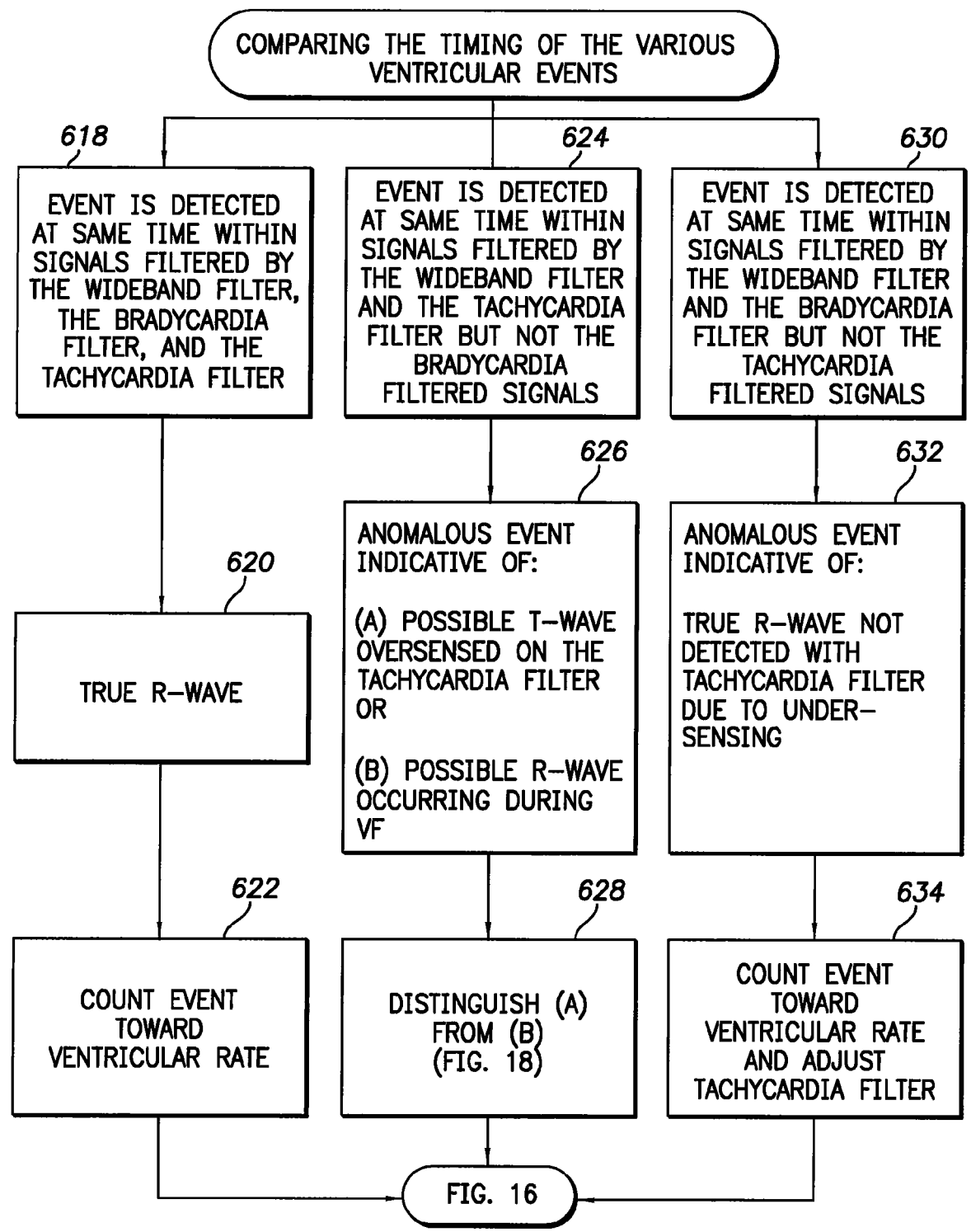
FIG. 17 particularly illustrates techniques for comparing the timing of events detected using the three filters to distinguish true R-waves from other events for use with the embodiment of FIG. 16.

Turning now to FIG. 17, an exemplary technique for identifying true R-waves will be described for use at step 612 of FIG. 16. At step 618, the pacer/ICD detects circumstances wherein an event is detected at the same time within signals filtered by the wideband filter, the bradycardia filter, and the tachycardia filter. That is, an event is detected substantially simultaneously using all three filters. In this case, the event is regarded as being a true R-wave, at step 620, and is counted toward the ventricular rate at step 622. In this regard, for an event to appear on all three filtered signals at the same time, the event almost certainly must be a true R-wave. If it were another event, such as a T-wave, it would not have appeared on the bradycardia-filtered signal. Meanwhile, at step 624, the pacer/ICD detects circumstances wherein an event is detected at the same time within signals filtered by the wideband filter and the tachycardia filter but not the bradycardia filter. In this case, the event is regarded, at step 626, as being an anomalous event indicative of: (a) a possible T-wave oversensed on the tachycardia filter or (b) a possible R-wave occurring during VF. In this regard, for an event to appear on the wideband and tachycardia filtered signals at the same time but not on the bradycardia filtered signals, it is either a T-wave that is being oversensed by the tachycardia (while being properly filtered out by the bradycardia filter), or it is a very high rate VF R-wave that the tachycardia filter is detecting but that is at too high a rate for the bradycardia filter to detect. Step 628 is performed to distinguish (a) from (b). The techniques of FIG. 18, discussed below, maybe employed at step 628.

Still further, at step 630, the pacer/ICD detects circumstances wherein an event is detected at the same time within signals filtered by the wideband filter and the bradycardia filter but not the tachycardia filter. In this case, the event is regarded, at step 632, as being an anomalous event indicative of: a true R-wave not detected with tachycardia filter due to under-sensing by that filter. In this regard, for an event to appear on the wideband and bradycardia filtered signals at the same time, it must be a low rate R-wave. Low rate R-waves should also be detected by the tachycardia filter. Hence, if the low rate R-wave is not detected on the tachycardia filter, it is likely due to undersensing by that filter. That is, the sensitivity of the tachycardia filter is set to low. Accordingly, at step 634, the pacer/ICD counts the event toward ventricular rate and adjusts tachycardia filter in an attempt to reduce or eliminate the tachycardia filter undersensing.

Turning now to FIG. 18, an exemplary technique is provided for distinguishing T-waves oversensed on the tachycardia filter from R-waves occurring during VF, for use at step 628 of FIG. 17. As noted, this processing is triggered if an event is detected at the same time by the wideband filter and by tachycardia filter but not by the bradycardia filter. At step 636, the pacer/ICD determines a ventricular rate from the wideband filtered signals only and then determines, at step 638, whether the wideband ventricular rate is consistent with VF. To be able to determine whether the wideband ventricular rate is consistent with VF, the pacer/ICD may, for example, periodically track the wideband-filtered rate and record that information. The pacer/ICD examines recent values of the wideband-filtered rate and, if the wideband-filtered rate had recently increasing very rapidly, then such would be consistent with VF. (Note that a high wideband rate, by itself, is not necessarily indicative of VF, since the high rate might be due to substantial oversensing within the wideband-filtered signals.)

In any case, if the wideband-filtered rate is consistent with VF, then the anomalous event of step 626 of FIG. 17 is likely an R-wave occurring during VF, i.e. an R-wave occurring at a rate too high for the bradycardia filter to detect. Accordingly, at step 640, the pacer/ICD identifies the anomalous event as being an R-wave occurring during possible VF and is counted toward the ventricular rate. At step 642, the bradycardia-filtered signals are ignored and, at step 644, the possible VF is verified using only tachycardia filtered signals. For example, a ventricular rate derived exclusively from tachycardia-filtered signals may be compared against a VF rate threshold. If it exceeds the threshold, VF is verified and one or more defibrillation shocks are immediately delivered in an effort to revert the heart to a normal sinus rhythm, at step 646. If VF is not verified, it is still possible that VT is occurring and so processing returns to FIG. 17 and hence to FIG. 16 so that the ventricular rate can be compared against a VT threshold (step 614) and appropriate VT therapy delivered (step 616.)

On the other hand, if the wideband-filtered rate determined at step 636 is not consistent with VF, then the anomalous event of step 626 of FIG. 17 is likely the result of T-wave oversensing, i.e. a T-wave being erroneously detected by the tachycardia filter. Accordingly, at step 648, the pacer/ICD identifies the anomalous event as being an oversensed T-wave. The event is not counted toward ventricular rate. The pacer/ICD preferably adjusts the tachycardia filter sensitivity so as to prevent or reduce further T-wave oversensing. Even in the presence of T-wave oversensing, it is still possible that VT is occurring and so processing likewise returns to FIG. 17 and hence to FIG. 16 so that the ventricular rate can be compared against the VT threshold (step 614) and appropriate VT therapy can be delivered (step 616.)

The logic of FIGS. 16-18 is summarized in Table II, above. Although not shown in the figures, any event not detected using either the bradycardia filter or the tachycardia filter, but which is detected using the wideband filter is noise or is a far-field P-wave, and is ignored for the purposes of ventricular rate calculation. Likewise, in the unlikely event that an event is detected on both the bradycardia and tachycardia filters but not on the wideband filter, that event is ignored as an anomalous event, likely arising due to noise on the bradycardia and tachycardia channels.

Thus, FIGS. 5-18 illustrate various techniques for detecting ventricular tachyarrhythmia. Depending up on the implementation, the techniques may be implemented separately or, in some cases, may be implemented together. That is, pacer/ICDs may be provided that combine two or more of the exemplary techniques for use in the detection and confirmation of tachyarrhythmias. For example, in some implementations, therapy is delivered if any of the various techniques detect and confirm ventricular tachyarrhythmia. In other implementations, therapy is delivered only if each of the techniques detects and confirms ventricular tachyarrhythmia. As can be appreciated, a variety of combinations of the various techniques are available in accordance with the invention and such combinations will not be described further.

Overview of T-Wave Oversensing Detection Techniques

Turning now to FIGS. 19-22, techniques for detecting T-wave oversensing will be summarized, wherein the techniques use the narrowband tachycardia filter and the narrowband bradycardia filter and, in some examples, additionally use the wideband filter. These T-wave oversensing detection techniques have already been described and discussed in connection with the tachyarrhythmia detection techniques above. It should be understood, however, that the T-wave oversensing detection techniques can be used independently, i.e. the techniques need not be exploited only in furtherance of tachyarrhythmia detection. Accordingly, for the sake of completeness, FIGS. 19-22 are provided to set forth the T-wave oversensing techniques independently of the tachyarrhythmia detection techniques. Since these techniques have already been described and discussed, detailed descriptions will not be provided again. Rather, the techniques will only be summarized.

Figure 19:
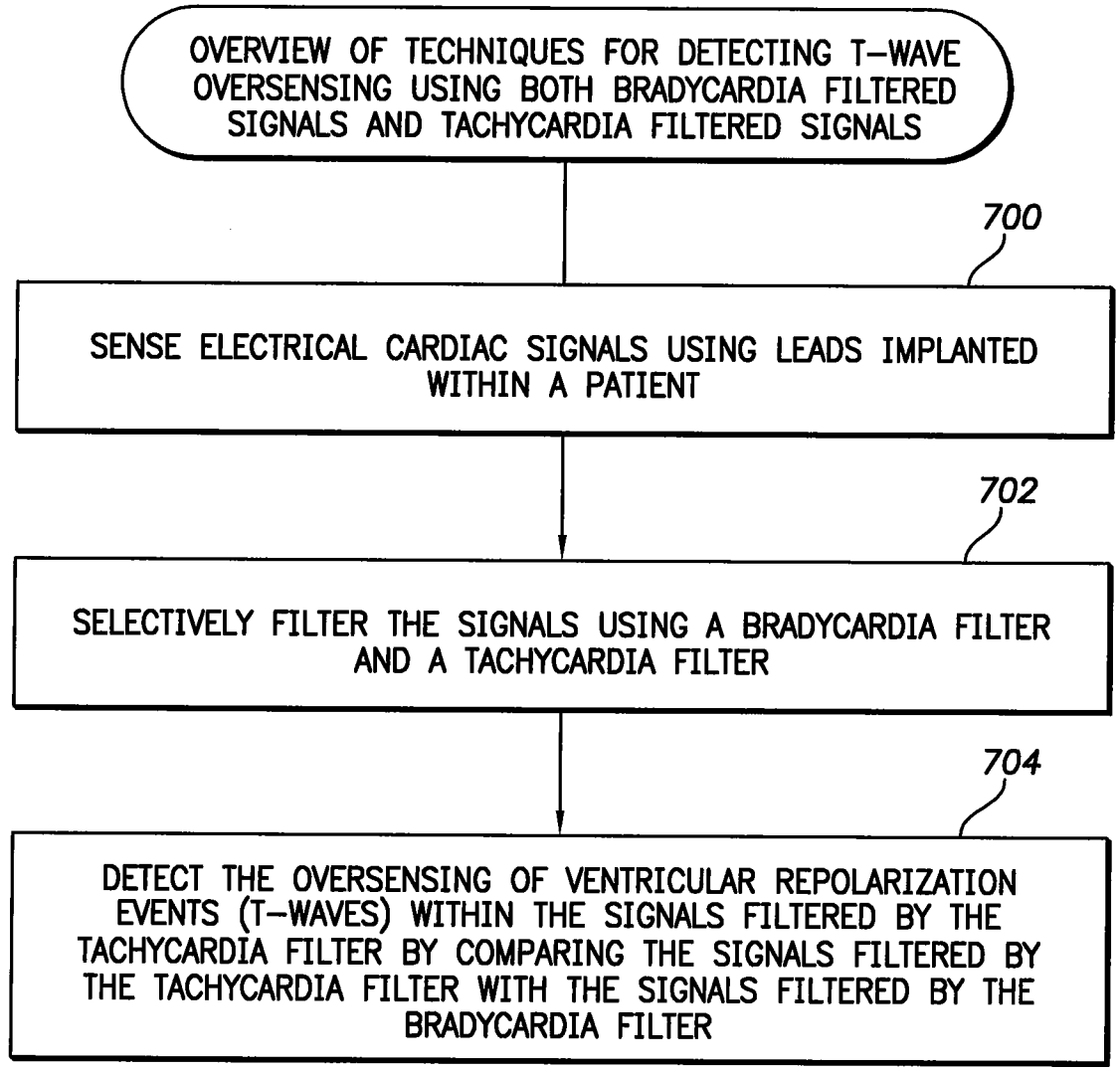
FIG. 19 provides an overview of a technique performed by the system of FIG. 4 for detecting T-wave oversensing using a bradycardia filter in combination with a tachycardia filter.

FIG. 19 provides a broad overview of the techniques for detecting T-wave oversensing using both bradycardia filtered signals and tachycardia-filtered signals. At step 700, the pacer/ICD senses electrical cardiac signals using leads implanted within a patient. At step 702, the pacer/ICD selectively filters the signals using a bradycardia filter and a tachycardia filter. At step 704, the pacer/ICD detects the oversensing of ventricular repolarization events (T-waves) within the signals filtered by the tachycardia filter by comparing the signals filtered by the tachycardia filter with the signals filtered by the bradycardia filter. Preferably, if T-wave oversensing is detected, the oversensed T-waves are rejected for the purposes of calculating the ventricular rate, triggering or inhibiting therapy, etc. Also, preferably, the sensitivity of the tachycardia filter is adjusted so to reduce or eliminate further T-wave oversensing.

Note that, whereas the techniques of FIG. 19 are preferably employed in "real time" based on IEGM signals as they are sensed, the techniques can alternatively be employed based on previously recorded signals. For example, IEGM data may be collected over time then analyzed later to detect T-wave oversensing that may have already occurred for the purpose of generate appropriate diagnostic data for physician review. Such delayed analysis techniques can be performed either using the implanted device itself or using an external data processing device based on data transmitted from the implanted device. Real time detection is preferred as it allows T-wave oversensing to be promptly detected so that appropriate action can be taken.

Figure 20:
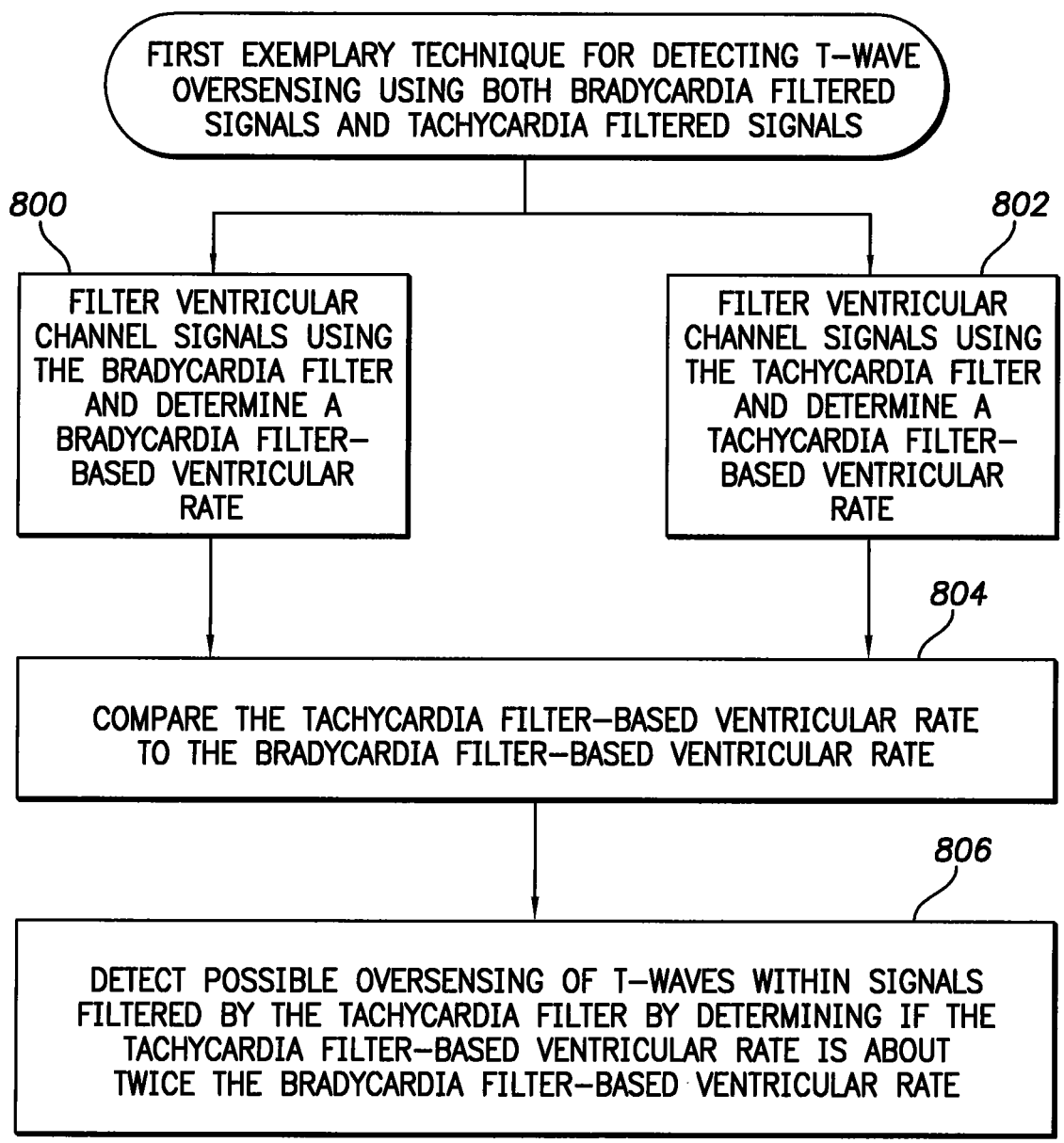
FIG. 20 illustrates a first illustrative example of the T-wave oversensing technique of FIG. 19, wherein T-wave oversensing is detected if a tachycardia filter-based ventricular rate is about twice a bradycardia filter-based ventricular rate.
Figure 21:
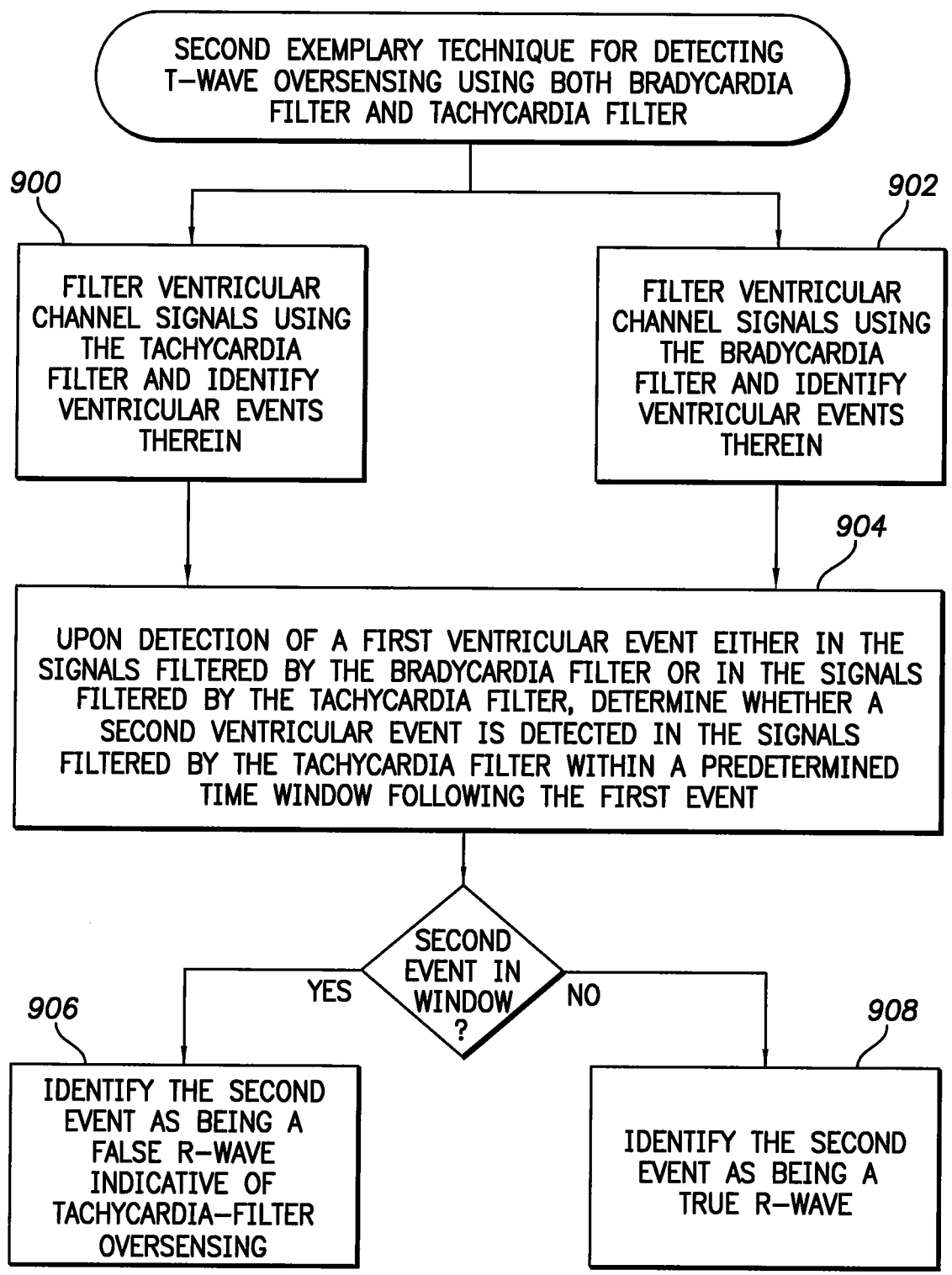
FIG. 21 illustrates a second illustrative example of the T-wave oversensing technique of FIG. 19, wherein a detection window is employed to detect T-wave oversensing.
Figure 22:
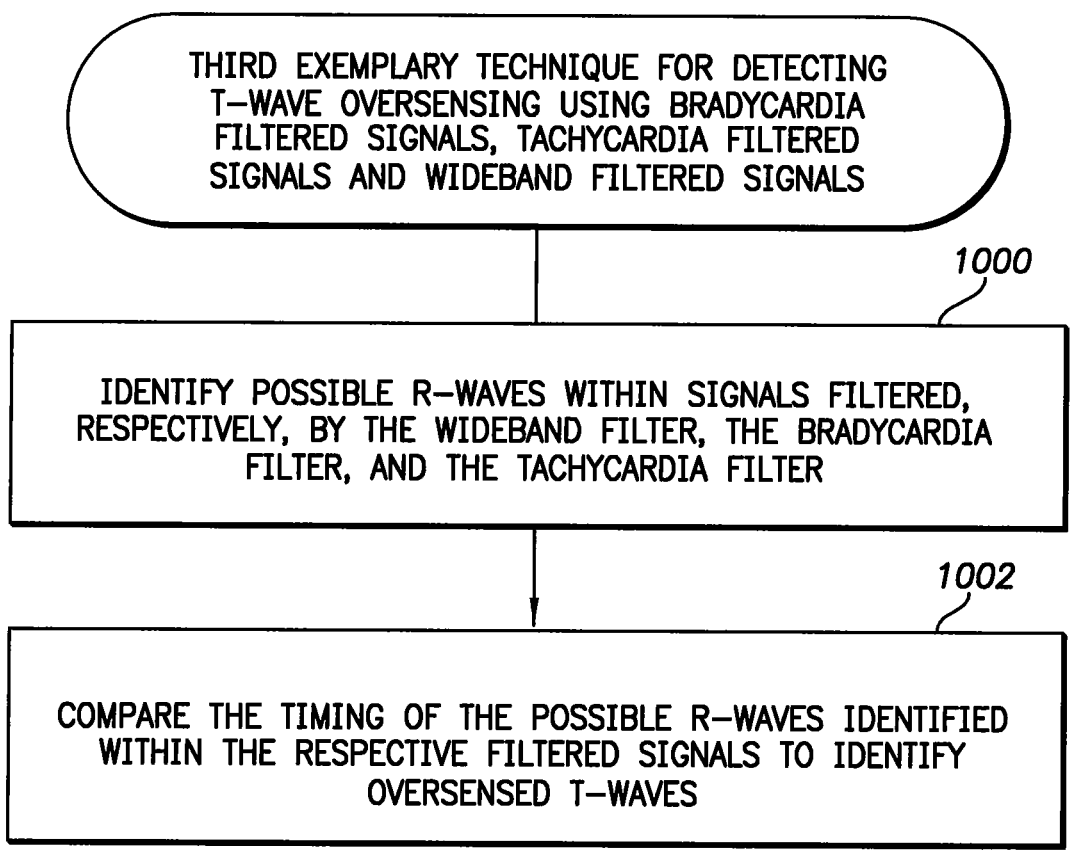
FIG. 22 illustrates a third illustrative example of the T-wave oversensing technique of FIG. 19, wherein signals filtered by a bradycardia filter, a tachycardia filter and a wideband filter are compared to detect T-wave oversensing.

FIGS. 20-22 summarize various exemplary techniques for performing the steps of FIG. 19.

First Exemplary T-Wave Oversensing Detection Technique

FIG. 20 illustrates a first exemplary T-wave oversensing detection technique, wherein T-wave oversensing is detected if a tachycardia filter-based ventricular rate is about twice a bradycardia filter-based ventricular rate. Beginning at step 800, the pacer/ICD filters ventricular channel signals using the bradycardia filter and determines a bradycardia filter-based ventricular rate. Concurrently, at step 802, the pacer/ICD filters ventricular channel signals using the tachycardia filter and determines a tachycardia filter-based ventricular rate. At step 804, the pacer/ICD compares the tachycardia filter-based ventricular rate to the bradycardia filter-based ventricular rate. At step 806, the pacer/ICD detects oversensing of T-waves within signals filtered by the tachycardia filter by determining if the tachycardia filter-based ventricular rate is about twice the bradycardia filter-based ventricular rate. For further descriptions of this T-wave oversensing detection technique see, e.g., Table I above, as well as the descriptions of FIGS. 9-11.

Second Exemplary T-Wave Oversensing Detection Technique

FIG. 21 illustrates the second exemplary T-wave oversensing detection technique, wherein a detection window is employed to detect T-wave oversensing. Beginning at step 900, the pacer/ICD filters ventricular channel signals using the tachycardia filter and identifies ventricular events therein. Concurrently, at step 904, the pacer/ICD filters ventricular channel signals using the bradycardia filter and identifies ventricular events therein. Upon detection of a first ventricular event either in the signals filtered by the bradycardia filter or in the signals filtered by the tachycardia filter, the pacer/ICD, at step 906, determines whether a second ventricular event is detected in the signals filtered by the tachycardia filter within a predetermined time window following the first event. If so, then, at step 906, the pacer/ICD identifies the second event as being a false R-wave indicative of tachycardia-filter oversensing. If not, then, at step 908, the pacer/ICD identifies the second event as being a true R-wave. For further descriptions of this T-wave oversensing detection technique see, e.g., the descriptions of FIG. 14.

Third Exemplary T-Wave Oversensing Detection Technique

FIG. 22 illustrates the third exemplary T-wave oversensing detection technique, wherein signals filtered by a bradycardia filter, a tachycardia filter and a wideband filter are compared to detect T-wave oversensing. Beginning at step 1000, the pacer/ICD identifies possible R-waves within signals filtered, respectively, by the wideband filter, the bradycardia filter, and the tachycardia filter. At step 1002, the pacer/ICD then compares the timing of the possible R-waves identified within the respective filtered signals to identify oversensed T-waves. For further descriptions of this T-wave oversensing detection technique, see, e.g., Table II above, as well as the descriptions of FIGS. 16-18.

Thus, FIGS. 19-22 illustrate various techniques for detecting T-wave oversensing. Depending up on the implementation, the techniques may be implemented separately or, in some cases, may be implemented together. That is, pacer/ICDs may be provided that combine two or more of the exemplary techniques for use in the detection of T-wave oversensing. As can be appreciated, a variety of combinations of the various techniques are available in accordance with the invention and such combinations will not be described further.

The various techniques discussed above may be implemented in any of a variety of implantable medical devices. For the sake of completeness, a detailed description of an exemplary pacer/ICD for performing these techniques will now be provided. However, principles of invention may be implemented within other pacer/ICD implementations or within other devices.

Exemplary Pacemaker/ICD

FIG. 23 provides a simplified block diagram of the pacer/ICD, which is a multi-chamber stimulation device capable of treating both fast and slow arrhythmias with stimulation therapy, including cardioversion, defibrillation, and pacing stimulation (as well as capable of detecting T-wave oversensing, detecting tachyarrhythmias, and delivering appropriate therapy.) To provide atrial chamber pacing stimulation and sensing, pacer/ICD 26 is shown in electrical communication with a heart 1112 by way of a left atrial lead 1120 having an atrial tip electrode 1122 and an atrial ring electrode 1123 implanted in the atrial appendage. Pacer/ICD 26 is also in electrical communication with the heart by way of a right ventricular lead 1130 having, in this embodiment, a ventricular tip electrode 1132, a right ventricular ring electrode 1134, a right ventricular (RV) coil electrode 1136, and a superior vena cava (SVC) coil electrode 1138. Typically, the right ventricular lead 1130 is transvenously inserted into the heart so as to place the RV coil electrode 1136 in the right ventricular apex, and the SVC coil electrode 1138 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 26 is coupled to a "coronary sinus" lead 1124 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 1124 is designed to receive atrial and ventricular cardiac signals and to deliver left ventricular pacing therapy using at least a left ventricular tip electrode 1126, left atrial pacing therapy using at least a left atrial ring electrode 1127, and shocking therapy using at least a left atrial coil electrode 1128. With this configuration, biventricular pacing can be performed. Although only three leads are shown in FIG. 23, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 24:
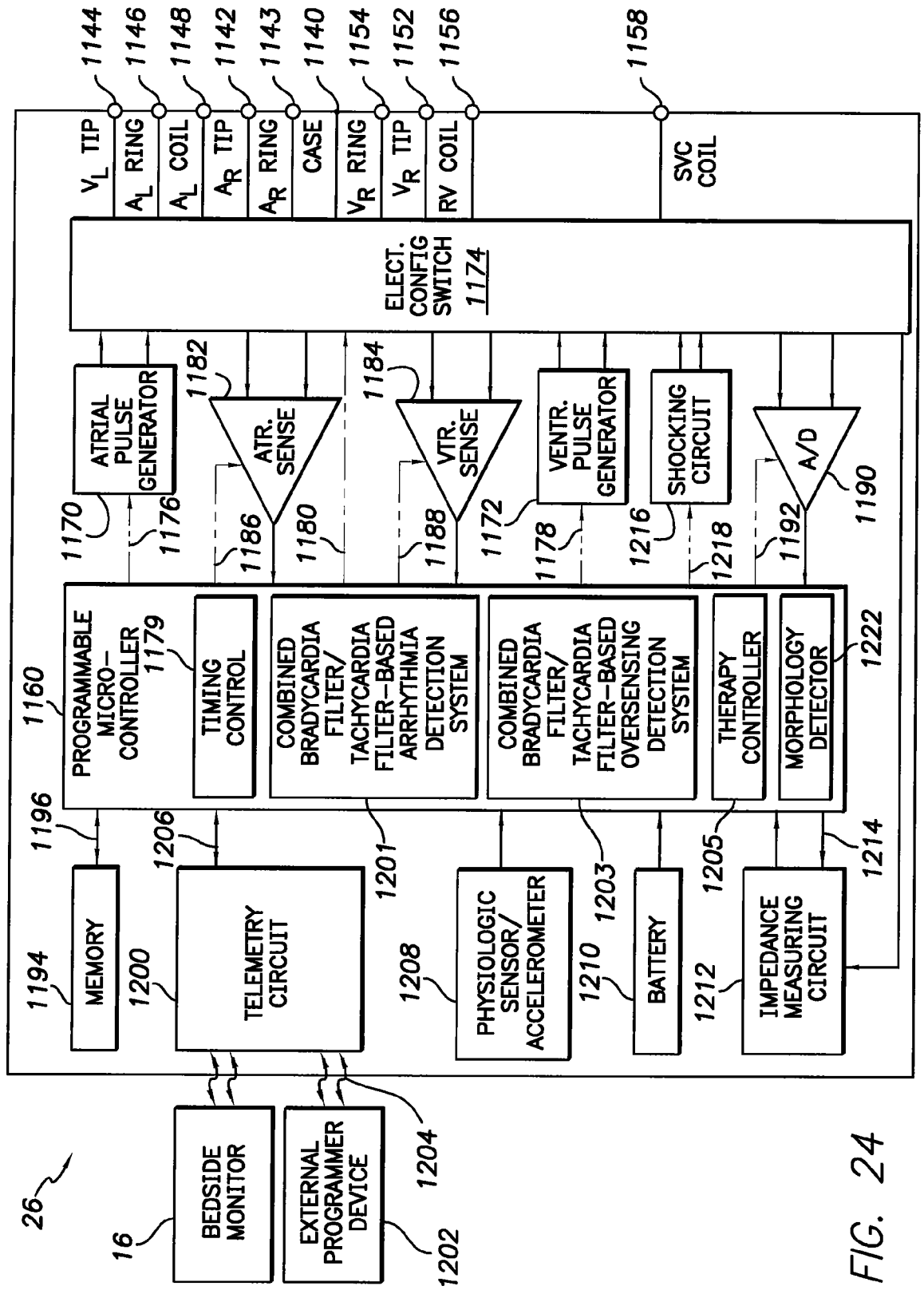
FIG. 24 is a functional block diagram of the pacer/ICD of FIG. 23, illustrating basic circuit elements that provide cardioversion, defibrillation and/or pacing stimulation in four chambers of the heart and particularly illustrating an components for detecting tachyarrhythmias and detecting T-wave oversensing in accordance with the techniques of FIGS. 5-22.

A simplified block diagram of internal components of pacer/ICD 26 is shown in FIG. 24. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 1140 for pacer/ICD 26, shown schematically in FIG. 24, is often referred to as the "can"", case" or "case electrode" and may be programmably selected to act as the return electrode for all "unipolar" modes. The housing 1140 may further be used as a return electrode alone or in combination with one or more of the coil electrodes, 1128, 1136 and 1138, for shocking purposes. The housing 1140 further includes a connector (not shown) having a plurality of terminals, 1142, 1143, 1144, 1146, 1148, 1152, 1154, 1156 and 1158 (shown schematically and, for convenience, the names of the electrodes to which they are connected are shown next to the terminals). As such, to achieve right atrial sensing and pacing, the connector includes at least a right atrial tip terminal ($A_R$ TIP) 1142 adapted for connection to the atrial tip electrode 1122 and a right atrial ring ($A_R$ RING) electrode 1143 adapted for connection to right atrial ring electrode 1143. To achieve left chamber sensing, pacing and shocking, the connector includes at least a left ventricular tip terminal ($V_L$ TIP) 1144, a left atrial ring terminal ($A_L$ RING) 1146, and a left atrial shocking terminal ($A_L$ COIL) 1148, which are adapted for connection to the left ventricular ring electrode 1126, the left atrial tip electrode 1127, and the left atrial coil electrode 1128, respectively. To support right chamber sensing, pacing and shocking, the connector further includes a right ventricular tip terminal ($V_R$ TIP) 1152, a right ventricular ring terminal ($V_R$ RING) 1154, a right ventricular shocking terminal ($R_V$ COIL) 1156, and an SVC shocking terminal (SVC COIL) 1158, which are adapted for connection to the right ventricular tip electrode 1132, right ventricular ring electrode 1134, the RV coil electrode 1136, and the SVC coil electrode 1138, respectively. Separate terminals (not shown) may be provided for connecting the implanted warning device 14 and the implanted drug pump 18, which are instead shown coupled directly to internal functional components of the pacer/ICD that control these devices.

At the core of pacer/ICD 26 is a programmable microcontroller 1160, which controls the various modes of stimulation therapy. As is well known in the art, the microcontroller 1160 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 1160 includes the ability to process or monitor input signals (data) as controlled by a program code stored in a designated block of memory. The details of the design and operation of the microcontroller 1160 are not critical to the invention. Rather, any suitable microcontroller 1160 may be used that carries out the functions described herein. The use of microprocessor-based control circuits for performing timing and data analysis functions are well known in the art.

As shown in FIG. 24, an atrial pulse generator 1170 and a ventricular/impedance pulse generator 1172 generate pacing stimulation pulses for delivery by the right atrial lead 1120, the right ventricular lead 1130, and/or the coronary sinus lead 1124 via an electrode configuration switch 1174. It is understood that in order to provide stimulation therapy in each of the four chambers of the heart, the atrial and ventricular pulse generators, 1170 and 1172, may include dedicated, independent pulse generators, multiplexed pulse generators or shared pulse generators. The pulse generators, 1170 and 1172, are controlled by the microcontroller 1160 via appropriate control signals, 1176 and 1178, respectively, to trigger or inhibit the stimulation pulses.

The microcontroller 1160 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 1174 includes a plurality of switches for connecting the desired electrodes to the appropriate I/O circuits, thereby providing complete electrode programmability. Accordingly, the switch 1174, in response to a control signal 1180 from the microcontroller 1160, determines the polarity of the stimulation pulses (e.g., unipolar, bipolar, combipolar, etc.) by selectively closing the appropriate combination of switches (not shown) as is known in the art.

Atrial sensing circuits 1182 and ventricular sensing circuits 1184 may also be selectively coupled to the right atrial lead 1120, coronary sinus lead 1124, and the right ventricular lead 1130, through the switch 1174 for detecting the presence of cardiac activity in each of the four chambers of the heart. Accordingly, the atrial (ATR. SENSE) and ventricular (VTR. SENSE) sensing circuits, 1182 and 1184, may include dedicated sense amplifiers, multiplexed amplifiers or shared amplifiers. The switch 1174 determines the "sensing polarity" of the cardiac signal by selectively closing the appropriate switches, as is also known in the art. In this way, the clinician may program the sensing polarity independent of the stimulation polarity. Each sensing circuit, 1182 and 1184, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 1182 and 1184, are connected to the microcontroller 1160 which, in turn, are able to trigger or inhibit the atrial and ventricular pulse generators, 1170 and 1172, respectively, in a demand fashion in response to the absence or presence of cardiac activity in the appropriate chambers of the heart.

The ventricular sense amplifier 1184 preferably includes the aforementioned bradycardia filter, tachycardia filter and wideband filter, shown separately in FIG. 25, discussed below.

For arrhythmia detection, pacer/ICD 26 utilizes the atrial and ventricular sensing circuits, 1182 and 1184, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 1160 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 1190. The data acquisition system 1190 is configured to acquire intracardiac electrogram signals, convert the raw analog data into a digital signal, and store the digital signals for later processing and/or telemetric transmission to an external device 1202. The data acquisition system 1190 is coupled to the right atrial lead 1120, the coronary sinus lead 1124, and the right ventricular lead 1130 through the switch 1174 to sample cardiac signals across any pair of desired electrodes. The microcontroller 1160 is further coupled to a memory 1194 by a suitable data/address bus 1196, wherein the programmable operating parameters used by the microcontroller 1160 are stored and modified, as required, in order to customize the operation of pacer/ICD 26 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart. Other pacing parameters include base rate, rest rate and circadian base rate.

Advantageously, the operating parameters of the implantable pacer/ICD 26 may be non-invasively programmed into the memory 1194 through a telemetry circuit 1200 in telemetric communication with the external device 1202, such as a programmer, transtelephonic transceiver or a diagnostic system analyzer. The telemetry circuit 1200 is activated by the microcontroller by a control signal 1206. The telemetry circuit 1200 advantageously allows intracardiac electrograms and status information relating to the operation of pacer/ICD 26 (as contained in the microcontroller 1160 or memory 1194) to be sent to the external device 1202 through an established communication link 1204. Pacer/ICD 26 further includes an accelerometer or other physiologic sensor 1208, commonly referred to as a "rate-responsive" sensor because it is typically used to adjust pacing stimulation rate according to the exercise state of the patient. However, the physiological sensor 1208 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 1160 responds by adjusting the various pacing parameters (such as rate, AV Delay, V-V Delay, etc.) at which the atrial and ventricular pulse generators, 1170 and 1172, generate stimulation pulses. While shown as being included within pacer/ICD 26, it is to be understood that the sensor 1208 may also be external to pacer/ICD 26, yet still be implanted within or carried by the patient. A common type of rate responsive sensor is an activity sensor incorporating an accelerometer or a piezoelectric crystal, which is mounted within the housing 1140 of pacer/ICD 26. Other types of physiologic sensors are also known, for example, sensors that sense the oxygen content of blood, respiration rate and/or minute ventilation, pH of blood, ventricular gradient, etc.

The pacer/ICD additionally includes a battery 1210, which provides operating power to all of the circuits shown in FIG. 24. The battery 1210 may vary depending on the capabilities of pacer/ICD 26. If the system only provides low voltage therapy, a lithium iodine or lithium copper fluoride cell may be utilized. For pacer/ICD 26, which employs shocking therapy, the battery 1210 should be capable of operating at low current drains for long periods, and then be capable of providing high-current pulses (for capacitor charging) when the patient requires a shock pulse. The battery 1210 should also have a predictable discharge characteristic so that elective replacement time can be detected. Accordingly, pacer/ICD 26 is preferably capable of high voltage therapy and batteries or other power sources appropriate for that purpose are employed.

As further shown in FIG. 24, pacer/ICD 26 is shown as having an impedance measuring circuit 1212 which is enabled by the microcontroller 1160 via a control signal 1214. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 124 so that any desired electrode may be used.

In the case where pacer/ICD 26 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 1160 further controls a shocking circuit 1216 by way of a control signal 1218. The shocking circuit 1216 generates shocking pulses of low (up to 0.5 joules), moderate (0.5-10 joules) or high energy (11 to 40 joules), as controlled by the microcontroller 1160. Such shocking pulses are applied to the heart of the patient through at least two shocking electrodes, and as shown in this embodiment, selected from the left atrial coil electrode 1128, the RV coil electrode 1136, and/or the SVC coil electrode 1138. The housing 1140 may act as an active electrode in combination with the RV electrode 1136, or as part of a split electrical vector using the SVC coil electrode 1138 or the left atrial coil electrode 1128 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 1160 is capable of controlling the synchronous or asynchronous delivery of the shocking pulses.

Microcontroller 110 also includes a combined bradycardia filter/tachycardia filter-based arrhythmia detection system 1201 operative to detect tachyarrhythmia within the patient using signals filtered by the bradycardia filter in combination with the signals filtered by the tachycardia filter, in accordance with the techniques summarized in FIG. 5. The microcontroller also includes a combined bradycardia filter/tachycardia filter-based oversensing detection system 1203 operative to detect the oversensing of ventricular repolarization events within the signals filtered by the tachycardia filter by comparing the signals filtered by the tachycardia filter with the signals filtered by the bradycardia filter, in accordance with the techniques summarized in FIG. 19. Therapy provided in response to any detected arrhythmias is controlled by a therapy controller 1205. Depending upon the implementation, the various components illustrated within the microcontroller may be implemented as separate hardware or software modules. However, the modules may be combined so as to permit single modules to perform multiple functions.

Figure 25:
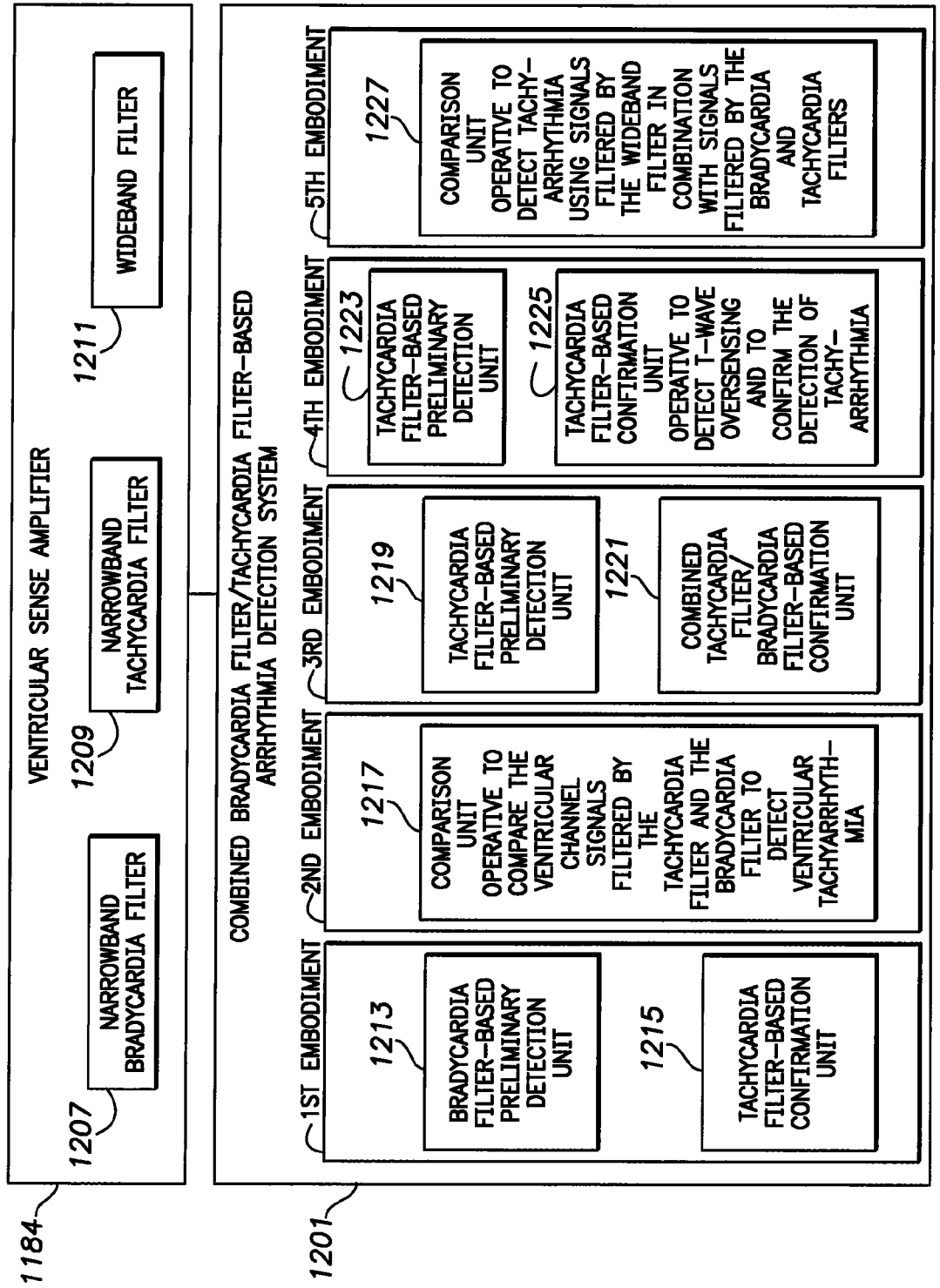
FIG. 25 is a functional block diagram of pertinent components of the pacer/ICD of FIG. 24, particularly illustrating components for detecting tachyarrhythmias in accordance with the techniques of FIGS. 5-18.

FIG. 25 illustrates, in block diagram form, pertinent components of the ventricular sense amplifier 1184 and the combined bradycardia filter/tachycardia filter-based arrhythmia detection system 1201 of FIG. 24, and particular illustrating pertinent sub-components thereof. Briefly, ventricular sense amplifier 1184 includes the bradycardia filter 1207, the tachycardia filter 1209 and the wideband filter 1211. The combined bradycardia filter/tachycardia filter-based arrhythmia detection system 1201 includes various components directed to the various illustrative embodiments described above. It should be understood that the typical combined bradycardia filter/tachycardia filter-based arrhythmia detection system will not include each of the components but may be equipped, for example, with only one of the set of components corresponding to whichever particular embodiment is implemented. Briefly, the arrhythmia detection system may include first embodiment components including a bradycardia filter-based preliminary detection unit 1213 operative to detect a preliminary indication of tachyarrhythmia using signals filtered by the bradycardia filter and a tachycardia filter-based confirmation unit 1215 operative to confirm the detection of tachyarrhythmia using signals filtered by the tachycardia filter, generally in accordance with the techniques of FIGS. 6-8, discussed above. The arrhythmia detection system may additionally or alternatively include second embodiment components including a comparison unit 1217 operative to compare the ventricular channel signals filtered by the tachycardia filter and the bradycardia filter to detect ventricular tachyarrhythmia, generally in accordance with the techniques of FIGS. 9-11, discussed above.

The arrhythmia detection system may additionally or alternatively include third embodiment components including a tachycardia filter-based preliminary detection unit 1219 operative to detect a preliminary indication of tachyarrhythmia using signals filtered by the tachycardia filter; and a bradycardia/tachycardia filter-based confirmation unit 1221 operative to then confirm the detection of tachyarrhythmia using signals filtered by the bradycardia filter and the tachycardia filter, generally in accordance with the techniques of FIG. 12, discussed above. The arrhythmia detection system may additionally or alternatively include fourth embodiment components including a tachycardia filter-based preliminary detection unit 1223 operative to detect a preliminary indication of tachyarrhythmia using signals filtered by the bradycardia filter; and a tachycardia filter-based confirmation unit 1225 operative to detect oversensing of ventricular repolarization events by the tachycardia filter and to confirm the detection of tachyarrhythmia only in the absence of oversensing of ventricular repolarization events, generally in accordance with the techniques of FIGS. 13-15, discussed above. The arrhythmia detection system may additionally or alternatively include fifth embodiment components including a comparison unit 1227 operative to detect tachyarrhythmia using signals filtered by the wideband filter in combination with signals filters by the bradycardia and tachycardia filters, generally in accordance with the techniques of FIGS. 16-18, discussed above.

Figure 26:
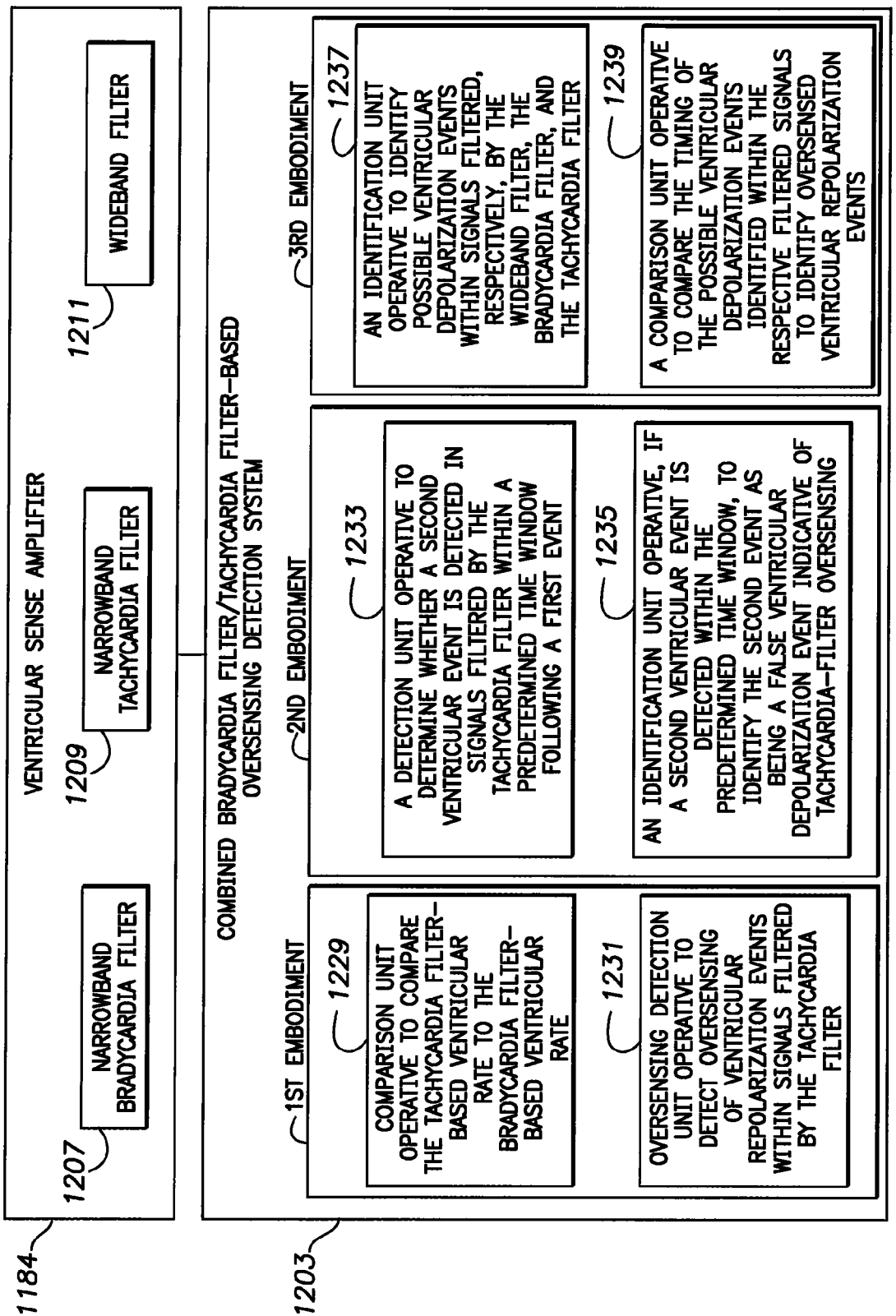
FIG. 26 is a functional block diagram of pertinent components of the pacer/ICD of FIG. 24, particularly illustrating components for detecting T-wave oversensing in accordance with the techniques of FIGS. 19-22.

FIG. 26 illustrates, in block diagram form, pertinent components of the ventricular sense amplifier 1184 and the combined bradycardia filter/tachycardia filter-based oversensing detection system 1203 of FIG. 24, and particular illustrating pertinent sub-components thereof. As before, the ventricular sense amplifier 1184 includes the bradycardia filter 1207, the tachycardia filter 1209 and the wideband filter 1211. The combined bradycardia filter/tachycardia filter-based oversensing detection system 1203 includes various components directed to the various illustrative embodiments described above. It should again be understood that the typical combined bradycardia filter/tachycardia filter-based oversensing detection system will not include each of the components but may be equipped, for example, with only one of the set of components corresponding to whichever particular embodiment is implanted. Briefly, the oversensing detection system may include first embodiment components including a comparison unit 1229 operative to compare the tachycardia filter-based ventricular rate to the bradycardia filter-based ventricular rate; and an oversensing detection unit 1231 operative to detect oversensing of ventricular repolarization events within signals filtered by the tachycardia filter by determining if the tachycardia filter-based ventricular rate is about twice the bradycardia filter-based ventricular rate, generally in accordance with the techniques of FIG. 20, discussed above.

The oversensing detection system may additionally or alternatively include second embodiment components including a detection unit 1233 operative, upon detection of a first ventricular event either in signals filtered by the bradycardia filter or in signals filtered by the tachycardia filter, to determine whether a second ventricular event is detected in the signals filtered by the tachycardia filter within a predetermined time window following the first event; and an identification unit 1235 operative, if a second ventricular event is detected within the predetermined time window, to identify the second event as being a false ventricular depolarization event indicative of tachycardia-filter oversensing, and operative, if a second ventricular event is not detected within the predetermined time window, to identify the second event as being indicative of a true ventricular depolarization event, generally in accordance with the techniques of FIG. 21, discussed above.

The oversensing detection system may additionally or alternatively include third embodiment components including an identification unit 1237 operative to identify possible ventricular depolarization events within signals filtered, respectively, by the wideband filter, the bradycardia filter, and the tachycardia filter, and a comparison unit 1239 operative to compare the timing of the possible ventricular depolarization events identified within the respective filtered signals to identify oversensed ventricular repolarization events, generally in accordance with the techniques of FIG. 22, discussed above.

What have been described are various exemplary systems and methods for use with an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the scope of the invention. Note also that the term "including" as used herein is intended to be inclusive, i.e. "including but not limited to".

What is claimed is:

1. A method comprising:
    sensing electrical cardiac signals via leads implanted within a heart of a patient;
    filtering the signals using a first filter configured to substantially eliminate signals having frequencies associated with ventricular repolarization events while retaining signals having frequencies associated with at least some ventricular depolarization events;
    filtering the signals using a second filter configured to pass signals having frequencies associated with ventricular depolarization events and ventricular repolarization events; and
    detecting tachyarrhythmia using a processor configured to detect tachyarrhythmia using ventricular depolarization events from signals filtered by the first filter in combination with ventricular rates determined from signals filtered by the second filter:
    wherein detecting tachyarrhythmia further comprises:
    detecting a preliminary indication of tachyarrhythmia using ventricular depolarization events from signals filtered by the first filter; and
    in response, confirming detection of tachyarrhythmia using the ventricular rates determined from signals filtered by the second filter.

2. The method of claim 1 wherein detecting a preliminary indication of tachyarrhythmia using ventricular depolarization events from signals filtered by the first filter comprises:

determining a ventricular rate based on the ventricular depolarization events; and comparing the ventricular rate to a detection threshold indicative of ventricular tachyarrhythmia.

3. The method of claim 1 further including delivering therapy in response to detecting tachyarrhythmia.

4. The method of claim 1 wherein the first filter is a bradycardia filter and the second filter is a tachycardia filter.

5. The method of claim 1 wherein the first filter has a passband beginning at 20 Hz and the second filter has a passband beginning at 10 Hz.

6. The method of claim 1 wherein detecting a preliminary indication of tachyarrhythmia using ventricular depolarization events from signals filtered by the first filter includes:
determining a ventricular morphology for the ventricular depolarizations; and
comparing the ventricular morphology to a criteria indicative of ventricular tachyarrhythmia.

7. The method of claim 6 wherein the ventricular morphology comprises at least one of R-wave shape and R-wave size and the criteria comprises a predetermined threshold number (X) of irregular shaped or irregular sized R-waves, out of a predetermined total number (Y) of R-waves.

8. The method of claim 1 wherein confirming detection of tachyarrhythmia comprises verifying that the ventricular rates determined from signals filtered by the second filter exceed a detection threshold indicative of ventricular tachyarrhythmia.

9. A method comprising:
sensing electrical cardiac signals via leads implanted within a heart of a patient;
filtering the signals using a first filter configured to substantially eliminate signals having frequencies associated with ventricular repolarization events while retaining signals having frequencies associated with at least some ventricular depolarization events;
filtering the signals using a second filter configured to pass signals having frequencies associated with ventricular depolarization events and ventricular repolarization events; and
detecting tachyarrhythmia using a processor configured to detect tachyarrhythmia using ventricular depolarization events from signals filtered by the first filter in combination with ventricular rates determined from signals filtered by the second filter;
wherein detecting tachyarrhythmia further comprises:
comparing the ventricular rates determined from signals filtered by the second filter with ventricular rates determined using ventricular depolarization events from signals filtered by the first filter to detect ventricular tachyarrhythmia.

10. The method of claim 9 further comprising:
prior to comparing ventricular rates determined from signals filtered by the second filter with ventricular rates determined from signals filtered by the first filter, comparing the ventricular rates determined from signals filtered by the second filter to a detection threshold indicative of ventricular tachyarrhythmia.

11. The method of claim 10 further comprising:
if the ventricular rates determined from signals filtered by the second filter exceed the threshold, comparing signals filtered by the first filter with signals filtered by the second filter to distinguish between true ventricular depolarization events and false ventricular depolarization events; and
detecting tachyarrhythmia based on the true ventricular depolarization events.

12. The method of claim 11 wherein detecting tachyarrhythmia based on the true ventricular depolarization events comprises:
determining a true ventricular rate based only on the true ventricular depolarization events; and
comparing the true ventricular rate to a detection threshold indicative of ventricular tachyarrhythmia.

13. The method of claim 11 wherein detecting tachyarrhythmia based on the true ventricular depolarization events comprises:
determining a count corresponding to the number of false ventricular depolarization events within a predetermined number of combined false ventricular depolarization events and true ventricular depolarization events; and
comparing the count to a count threshold indicative of indicative of tachyarrhythmia.

14. The method of claim 10 further comprising:
if the ventricular rates determined from signals filtered by the second filter exceed the threshold, then comparing ventricular rates determined from signals filtered by the second filter to a multiple of the ventricular rates determined from signals filtered by the first filter.

15. A method comprising:
sensing electrical cardiac signals via leads implanted within a heart of a patient;
filtering the signals using a first filter configured to substantially eliminate signals having frequencies associated with ventricular repolarization events while retaining signals having frequencies associated with at least some ventricular depolarization events;
filtering the signals using a second filter configured to pass signals having frequencies associated with ventricular depolarization events and ventricular repolarization events;
filtering the signals using a wideband filter configured to have a substantially wider bandwidth than the bandwidths of the first and second filters; and
detecting tachyarrhythmia using a processor configured to detect tachyarrhythmia using ventricular depolarization events from signals filtered by the first filter in combination with ventricular rates determined from signals filtered by the second filter;
wherein detecting tachyarrhythmia comprises detecting possible ventricular depolarization events in each of the signals filtered by the first filter, filtered by the second filter and filtered by the wideband filter; comparing the timing of the possible ventricular depolarization events to identify true ventricular depolarization events; calculating a true ventricular rate based on the identified true ventricular depolarizations; and comparing the true ventricular rate to a detection threshold.

16. A tachyarrhythmia detection system for use in an implantable medical device having filters for filtering electrical cardiac signals sensed via leads implanted within a heart of a patient, the system comprising:
a first filter configured to substantially eliminate signals having frequencies associated with ventricular repolarization events while retaining signals having frequencies associated with at least some ventricular depolarization events;
a second filter configured to pass signals having frequencies associated with ventricular depolarization events and ventricular repolarization events; and
a combined first filter/second filter-based arrhythmia detection system configured to detect tachyarrhythmia within the patient using ventricular depolarization events from signals filtered by the first filter in-combination with ventricular rates determined from signals filtered by the second filter;
wherein the combined first filter/second filter-based detection system includes:
a first filter-based preliminary detection unit configured to detect a preliminary indication of tachyarrhythmia using signals filtered by the first filter; and a second filter-based confirmation unit to then confirm detection of tachyarrhythmia using ventricular rates determined from signals filtered by the second filter.

17. A tachyarrhythmia detection system for use in an implantable medical device having filters for filtering electrical cardiac signals sensed via leads implanted within a heart of a patient, the system comprising:
   a first filter configured to substantially eliminate signals having frequencies associated with ventricular repolarization events while retaining signals having frequencies associated with at least some ventricular depolarization events;
   a second filter configured to pass signals having frequencies associated with ventricular depolarization events and ventricular repolarization events; and
   a combined first filter/second filter-based arrhythmia detection system configured to detect tachyarrhythmia within the patient using ventricular depolarization events from signals filtered by the first filter in-combination with ventricular rates determined from signals filtered by the second filter;
   wherein the combined first filter/second filter-based detection system includes a comparison unit configured to compare the ventricular rates determined from signals filtered by the second filter with ventricular rates determined from signals filtered by the first filter to detect ventricular tachyarrhythmia.

18. A tachyarrhythmia detection system for use in an implantable medical device having filters for filtering electrical cardiac signals sensed via leads implanted within a heart of a patient, the system comprising:
   a first filter configured to substantially eliminate signals having frequencies associated with ventricular repolarization events while retaining signals having frequencies associated with at least some ventricular depolarization events;
   a second filter configured to pass signals having frequencies associated with ventricular depolarization events and ventricular repolarization events; and
   a combined first filter/second filter-based arrhythmia detection system configured to detect tachyarrhythmia within the patient using ventricular depolarization events from signals filtered by the first filter in-combination with ventricular rates determined from signals filtered by the second filter;
   wherein the combined first filter/second filter-based detection system comprises:
   a second filter-based preliminary detection unit configured to detect a preliminary indication of tachyarrhythmia using signals filtered by the second filter; and
   a second filter-based confirmation unit configured to detect oversensing of ventricular repolarization events by the second filter and to confirm detection of tachyarrhythmia only in the absence of oversensing of ventricular repolarization events.

19. A tachyarrhythmia detection system for use in an implantable medical device having filters for filtering electrical cardiac signals sensed via leads implanted within a heart of a patient, the system comprising:
   a first filter configured to substantially eliminate signals having frequencies associated with ventricular repolarization events while retaining signals having frequencies associated with at least some ventricular depolarization events;
   a second filter configured to pass signals having frequencies associated with ventricular depolarization events and ventricular repolarization events; and
   a combined first filter/second filter-based arrhythmia detection system configured to detect tachyarrhythmia within the patient using ventricular depolarization events from signals filtered by the first filter in-combination with ventricular rates determined from signals filtered by the second filter;
   wherein the implantable device additionally includes a wideband filter having a substantially wider bandwidth than bandwidths of the first and second filters; and
   wherein the combined first filter/second filter-based detection system includes a comparison unit configured to detect tachyarrhythmia using signals filtered by the wideband filter in combination with signals filters by the first and second filters.

20. A tachyarrhythmia detection system for use in an implantable medical device having filters for filtering electrical cardiac signals sensed via leads implanted within a heart of a patient, the system comprising:
   means for sensing electrical cardiac signals within the patient;
   first means for filtering the signals to substantially eliminate signals having frequencies associated with ventricular repolarization events while retaining signals having frequencies associated with at least some ventricular depolarization events;
   second means for filtering the signals to pass signals having frequencies associated with ventricular depolarization events and ventricular repolarization events; and
   means for detecting tachyarrhythmia within the patient by comparing signals filtered by the second means for filtering with signals filtered by the first means for filtering.

* * * * *